(12) United States Patent
Willi et al.

(10) Patent No.: US 7,741,462 B2
(45) Date of Patent: Jun. 22, 2010

(54) FELINE HEMOPLASMA ISOLATE

(75) Inventors: Barbara Willi, Zurich (CH); Regina Hofmann-Lehmann, Rapperswil (CH); Hans Lutz, Rüdlingen (CH); Felicitas S. Boretti, Zurich (CH)

(73) Assignee: The University of Zurich Veterinary Clinical Laboratory, Zurich (CH)

( * ) Notice: Subject to any disclaimer, the term of this patent is extended or adjusted under 35 U.S.C. 154(b) by 387 days.

(21) Appl. No.: 11/417,979

(22) Filed: May 3, 2006

(65) Prior Publication Data

US 2006/0252080 A1 Nov. 9, 2006

Related U.S. Application Data

(60) Provisional application No. 60/677,383, filed on May 3, 2005.

(51) Int. Cl.
*C12Q 1/68* (2006.01)
*C07H 21/04* (2006.01)

(52) U.S. Cl. .................. 536/23.1; 536/24.3; 435/6; 435/91.2; 435/91.1

(58) Field of Classification Search ............... None
See application file for complete search history.

(56) References Cited

U.S. PATENT DOCUMENTS

| 6,204,003 | B1 * | 3/2001 | Steele et al. ............... 435/7.32 |
| 6,518,020 | B1 | 2/2003 | Jensen |
| 6,558,909 | B2 | 5/2003 | Jensen |
| 6,582,908 | B2 * | 6/2003 | Fodor et al. ............... 506/9 |

FOREIGN PATENT DOCUMENTS

WO    WO 99/14317    3/1999

OTHER PUBLICATIONS

NEB catalog (1998/1999), pp. 121, 284.*
Tanaka et al. (Genbank Accession AB113468, Feb. 1, 2005).*
Berent et al. (Infect. Immun. 71 (6), 3657-3662 (2003)).*
Willi (J. of Clin. Microbiology, vol. 45, No. 4, pp. 1159-1166, 2007).*
Willi et al. (J. Clinical Microbiology, vol. 43, No. 6, pp. 2581-2585, Jun. 2005).*
Willi et al. (J. Clinical Microbiology, vol. 44, No. 3, pp. 961-969, Mar. 2006).*
Willi et al. (Swiss Archive for Veterinary Medicine, vol. 148, No. 3, pp. 139-150, Mar. 2006).*
Berent, et al., "Detection of *Haemobartonella felis* in cats with experimentally induced acute and chronic infections, using a polymerase chain reaction assay", AJVR, vol. 59, No. 10, p. 1215-1220 (1998).
Foley, et al. "Molecular, clinical, and pathologic comparison of two distinct strains of *Haemobartonella felis* in domestic cats", AJVR, vol. 59, No. 12, p. 1581-1588 (1998).

Johansson, et al., "*Mycoplasma cavipharyngis* and *Mycoplasma fastidiosum*, the closest relatives to *Eperythrozoon* spp. and *Haemobartonella* spp.", FEMS Microbiology Letters 174, 321-326 (1999).
Westfall, et al., "Inoculation of two genotypes of *Hemobartonella felis* (California and Ohio variants) to induce infection in cats and the response to treatment with azithromycin", AJVR, vol. 62, No. 5, p. 687-691 (2001).
Bobade, et al., "A Comparative Study of the Efficiency of Acridine Orange and some Romanowsky Staining Procedures in the Demonstration of *Haemobartonella felis* in Feline Blood", Veterinary Parasitology, 26, 169-172 (1987).
Jensen, et al., "Use of a polymerase chain reaction assay to detect and differentiate two strains of *Haemobartonella felis* in naturally infected cats", AJVR, vol. 62, No. 4, p. 604-608 (2001).
Clark et al., "Detection of *Haemobartonella felis* (*Candidatus Mycoplasma haemofelis*) in Australia that is similar to the 'Ohio' strain", Aust. Vet. J. vol. 80, No. 11, p. 703-704 (2002).
Criado-Fornelio, et al., "Presence of *Mycoplasma haemofelis, Mycoplasma haemominutum* and piroplasmids in cats from southern Europe: a molecular study", Veterinary Microbiology, 93, 307-317 (2003).
Tasker, et al., "16S rDNA comparison demonstrates near identity between an United Kingdom *Haemobartonella felis* strain and the American California strain", Veterinary Microbiology, 81, 73-78 (2001).
Watanabe, et al., "Molecular Detection and Characterization of *Haemobartonella felis* in Domestic Cats in Japan Employing Sequence-Specific Polymerase Chain Reaction (SS-PCR)", J. Vet. Med. Sci. 65(10):1111-1114 (2003).
Maede, et al., "Studies on Feline *Haemobartonellosis* II. The mechanism of Anemia Produced by Infection with *Haemobartonella felis*", Jap. J. Vet. Sci. 37, p. 49-54 (1975).
Lobetti, et al., "Diagnosis of feline haemoplasma infection using a real-time PCR assay", Tydskr.S.Afr.vet.Ver. 75(2):94-99 (2004).
Cox, et al., "Autoimmune factors associated with anaemia in acute *Haemobartonella* and *Eperythrozoon* infections of rodents", Annals of Tropical Medicine and Parasitology, vol. 70, No. 1 p. 73-79 (1976).
Schilling, "Anaemia in mice caused by *Eperythrozoon coccoides*", Parasitology, p. 81-98 (1928).
Berkenkamp, et al., "Arthropod Transmission of *Eperythrozoon coccoides* in Mice", Laboratory Animal Science, vol. 38, No. 4, p. 398-401 (1988).
Flint, et al., "Feline Infectious Anemia. II. Experimental Cases", Am. J. Vet. Res., p. 33-40 (1959).
Leutenegger, et al., "Rapid feline immmunodeficiency virus provirus quantitation by polymerase chain reaction using the TaqMan® fluorogenic real-time detection system", Journal of Virological Methods78, p. 105-116 (1999).
Meli, et al., "High viral loads despite absence of clinical and pathological findings in cats experimentally infected with feline coronavirus (FCoV) type I and in naturally FCoV-infected cats", Journal of Feline Medicine and Surgery, 6, 69-81 (2004).

(Continued)

*Primary Examiner*—Jeanine A Goldberg
(74) *Attorney, Agent, or Firm*—McDonell Boehnen Hulbert & Berghoff LLP

(57) ABSTRACT

A newly identified hemoplasma agent, Candidatus *Mycoplasma turicensis*, is disclosed. Also disclosed are detection methods, screening methods and methods of diagnosis for the hemoplasma agent.

18 Claims, 3 Drawing Sheets

OTHER PUBLICATIONS

Messick, et al., "Development and Evaluation of a PCR-Based Assay for Detection of *Haemobartonella felis* in Cats and Differentiation of *H. felis* from Related Bacteria by Restriction Fragment Length Polymorphism Analysis", Journal of Clinical Microbiology, vol. 36, No. 2, p. 462-466 (1998).

Rikihisa, et al., "Western Immunblot Analysis of *Haemobartonella muris* and Comparison of 16S rRNA Gene Sequences of *H. muris, H. felis* and *Eperythrozoon suis*", Journal of Clinical Microbiology, p. 823-829 (1997).

Tasker, et al., "Phylogenetic Analysis of Hemoplams Species: an International Study", Journal of Clinical Microbiology, p. 3877-3880 (2003).

Neimark, et al., "Proposal to transfer some members of the genera *Haemobartonella* and *Eperythrozoon* to the genus Mycoplams with descriptions of '*Candidatus mycoplasma haemofelis*', '*Candidatus mycoplasma haemomuris*', *Candidatus mycoplasma haemosuis*' and '*Candidatus mycoplasma wenyonii*'", International Journal of Systematic and Evloutionary Microbiology, 51, 891-899 (2001).

Iralu, et al., "Agglutination of Mouse Erythrocytes by *Eperythrozoon coccoides*", Infection and Immunity, vol. 39, No. 2, p. 963-965 (1983).

Willi, et al., "Prevalence, Risk Factor Analysis, and Follow-Up of Infections Caused by Three Feline Hemoplasma Species in Cats in Switzerland", Journal of Clinical Microbiology, p. 961-969 (2006).

Hofmann-Lehmann, et al., "Feline leukaemia provirus load during the course of experimental infection and in naturally infected cats", Journal of General Virology, 82, 1589-1596 (2001).

Willi, et al., "Identification, Molecular Characterization, and Experimental Transmission of a New Hemoplasma Isolate from a Cat with Hemolytic Anemia in Switzerland", Journal of Clinical Microbiology, vol. 43, No. 6, p. 2581-2858 (2005).

Gen Bank Accession No. AY171918, May 9, 2005.
Gen Bank Accession No. HMU82963, Apr. 26, 1997.
Gen Bank Accession No. AY150973, Dec. 9, 2003.
Gen Bank Accession No. AY150985, Dec. 9, 2003.
Gen Bank Accession AF125878, May 26, 1999.
Gen Bank Accession AY297712, Jun. 22, 2003.
Gen Bank Accession AF338269, Oct. 21, 2002.
Gen Bank Accession AY532390, Mar. 7, 2005.
Gen Bank Accession AF016546, Nov. 18, 1997.
Gen Bank Accession AY492086, Dec. 27, 2003.
Gen Bank Accession AY831867, Jun. 20, 2005.

International Search Report dated Apr. 25, 2007 for corresponding application No. PCT/IB2006/002387.
GenBank Accession No. AY_171918 dated Jun. 3, 2003.
GenBank Accession No. U82963 dated Apr. 28, 1997.
GenBank Accession No. AY_150985 dated Nov. 30, 2002.
GenBank Accession No. AY_297712 dated Jun. 23, 2003.
GenBank Accession No. AY_529633 dated Sep. 10, 2004.
GenBank Accession No. BH_792926 dated Apr. 1, 2003.
GenBank Accession No. DQ_157156 dated Mar. 11, 2006.
GenBank Accession No. AC_111212 dated Feb. 22, 2002.
GenBank Accession No. AC_117126 dated Apr. 9, 2002.
GenBank Accession No. AC_166985 dated Aug. 14, 2005.
GenBank Accesion No. AC_135705 dated Oct. 24, 2002.

Willi, et al., "Identification, Molecular Characterization, and Experimental Transmission of a New Hemoplasma Isolate from a Cat with Hemolytic anemia in Switzerland", Journal of Clinical Microbiology, vol. 43, No. 6, p. 2581-2585, 2005.

Inokuma, et al., "Molecular Survey of *Mycoplasma haemofelis* and '*Candidatus mycoplasma haemominutum*' Infection in Cats in Yamaguchi and Surrounding Areas", J. Vet. Med. Sci. 66(8): 1017-1020, 2004.

Tasker, et al., "Use of Taqman PCR to determine the response of *Mycoplasma haemofelis* infection to antibiotic treatment", Journal of Microbiological Methods 56 (2004) 63-71.

Tasker, et al., "Use of Real-Time PCR to Detect and Quantify *Mycoplasma haemofelis* and "*Candidatus mycoplasma haemominutum*" DNA", Journal of Clinical Microbiology, vol. 41, No. 1, p. 439-441, 2003.

Tasker, et al., "Phylogenetic Analysis of Hemoplasma Species: an International Study", Journal of Clinical Microbiology, vol. 41, No. 8, p. 3877-3880, 2003.

Willi, et al., "Feline Haemoplasmen in der Schweiz: Identifikation einer neuen Spezies, Diagnose, Pravalenz und klinische Bedeutung", Band 148, Heft 3, p. 139-150, 2006.

Willi, et al., "Prevalence, Risk Factor Analysis, and Follow-Up of Infections Caused by Three Feline Hemoplasma Species in Cats in Switzerland", Journal of Clinical Microbiology, Vo. 44, No. 3, p. 961-969, 2006.

Willi, et al., "Phylogenetic Analysis of "*Candidatus Mycoplasma turicensis*" Isolates from Pet Cats in the United Kingdom, Australia, and South Africa, with Analysis of Risk Factors for Infection", Journal of Clinical Microbiology, vol. 44, No. 12, p. 4430-4435, 2006.

* cited by examiner

SEQUENCE LISTING

<160> NUMBER OF SEQ ID NOS: 19

<210> SEQ ID NO 1
<211> LENGTH: 23
<212> TYPE: DNA
<213> ORGANISM: Candidatus Mycoplasma turicensis

<400> SEQUENCE: 1
gaactgtcca aaaggcagtt agc                                         23

<210> SEQ ID NO 2
<211> LENGTH: 27
<212> TYPE: DNA
<213> ORGANISM: Candidatus Mycoplasma turicensis

<400> SEQUENCE: 2
agaagtttca ttcttgacac aattgaa                                     27

<210> SEQ ID NO 3
<211> LENGTH: 22
<212> TYPE: DNA
<213> ORGANISM: Candidatus Mycoplasma turicensis

<400> SEQUENCE: 3
gaaggccaga caggtcgtaa ag                                          22

<210> SEQ ID NO 4
<211> LENGTH: 25
<212> TYPE: DNA
<213> ORGANISM: Candidatus Mycoplasma turicensis

<400> SEQUENCE: 4
ctggcacata gttwgctgtc actta                                          25

<210> SEQ ID NO 5
<211> LENGTH: 1395
<212> TYPE: DNA
<213> ORGANISM: Candidatus Mycoplasma turicensis

<400> SEQUENCE: 5
cagaattaac gctggtggca tgcctaatac atgcaagtcg agcgaactgt ccaaaaggca    60
gttagcggcg aacgggtgag taatacatat ttaacatgcc ctccggaagg aaatagccgt   120
tcgaaagaac gattaatgtc ctatagtatc ctccatcaga cagaaggggg atttaaaggt   180
gaaaaccgcc ggaggattgg aatatgtcct attagctagt tggcgggata aaagcccacc   240
aaggcgatga taggtagctg gtctaagagg atgaacagcc acaatgggat tgagatacgg   300
cccatattcc tacgggaagc agcagtaggg aatcttccac aatgggcgaa agcctgatgg   360
agcaatgcca tgtgaacgat gaaggccaga caggtcgtaa agttctttta gaggggaaaa   420
atttgatggt accctctgaa taagtgacag caaactatgt gccagcagct gcggtaatac   480
ataggtcgcg agcgttattc ggatttattg ggcgtaaagc aagcgcaggc ggatgaataa   540
gttctgcatt aaaagcagct gcttaacagt tgtttgtgcc gaatactatt catctagaat   600
gtggtaggaa gttttggaat taaatatgga gcggtggaat gtgtagatat atttaagaac   660
accagaggcg aaggcgaaaa cttaggccat tattgacgct taggcttgaa agtgtgggta   720
gcaaatggga ttagataccc cagtagtcca caccgtaaac gatgggtatt agatgtcggg   780
atttgtgttt cggcgttgta gcttacgtgt taaataccccc gctgggtag tacatatgca   840 aatatgaaac tcaaaggaat tgacgggac ctgaacaagt ggtggaacat gttgcttaat   900
tcgataatac acgaaaaacc ttaccaaggt ttgacatcct ttgcaaagcc atagaaatat   960
ggtggaggtt atcagagtga caggtggtgc atggttgtcg tcagctcgtg tcatgagatg  1020
tttggttaag tcccgcaacg agcgcaaccc tactctttag ttgattgtct aaagagactg  1080
aacagtaatg tataggaagg atgggatcac gtcaaatcat catgccccctt atgccttggg  1140 ccgcaaacgt gttacaatgg tgagtacaat gtgtcgcgaa ccagcgatgg taagctaatc  1200
accaaaactc atctcagtcc ggataaaagg ctgcaattcg cctttttgaa gttggaatca  1260
ctagtaatcc cgtgtcagct atatcggggt gaatacgttc ccaggtcttg tacacaccgc  1320
ccgtcaaact atgagaggaa ggggcatttg aaaacacatt caattgtgtc aagaatgaaa  1380
cttctgattg gagtt                                                   1395

<210> SEQ ID NO 6
<211> LENGTH: 21
<212> TYPE: DNA
<213> ORGANISM: Candidatus Mycoplasma turicensis

<400> SEQUENCE: 6
aaatttgatg gtaccctctg a                                             21

<210> SEQ ID NO 7
<211> LENGTH: 1341
<212> TYPE: DNA

<213> ORGANISM: Candidatus Mycoplasma turicensis

<400> SEQUENCE: 7

```
gaactgtcca aaaggcagtt agcggcgaac gggtgagtaa tacatattta acatgccctc    60
cggaaggaaa tagccgttcg aaagaacgat taatgtccta tagtatcctc catcagacag   120
aaggggatt  taaaggtgaa accgccgga ggattggaat atgtcctatt agctagttgg   180
cgggataaaa gcccaccaag gcgatgatag gtagctggtc taagaggatg aacagccaca   240
atgggattga gatacggccc atattcctac gggaagcagc agtagggaat cttccacaat   300
gggcgaaagc ctgatggagc aatgccatgt gaacgatgaa ggccagacag gtcgtaaagt   360
tcttttagag gggaaaaatt tgatggtacc ctctgaataa gtgacagcaa attatgtgcc   420
agcagctgcg gtaatacata ggtcgcgagc gttattcgga tttattgggc gtaaagcaag   480
cgcaggcgga tgaataagtt ctgcattaaa agcagctgct taacagttgt tgtgccgaa    540
tactattcat ctagaatgtg gtaggaagtt ttggaattaa atatgagcg  gtggaatgtg   600
tagatatatt taagaacacc agaggcgaag gcgaaaactt aggccattat tgacgcttag   660
gcttgaaagt gtgggtagca aatgggatta gataccccag tagtccacac cgtaaacgat   720
gggtattaga tgtcgggatt tgtgtttcgg cgttgtagct tacgtgttaa ataccccgcc   780
tgggtagtac atatgcaaat atgaaactca aaggagttga cggggacctg aacaagtggt   840
ggaacatgtt gcttaattcg ataatacacg aaaaaccta  ccaaggtttg acatcctttg   900
caaagccata gaaatatggt ggaggttatc agagtgacag gtggtgcatg gttgtcgtca   960
gctcgtgtca tgagatgttt ggttaagtcc cgcaacgagc gcaaccctac tcttttagttg  1020
attgtctaaa gagactgaac agtaatgtat aggaaggatg ggatcacgtc aaatcatcat  1080
gcccttatg  ccttgggccg caaacgtgtt acaatggtga gtacaatgtg tcgcgaacca  1140
gcgatggtaa gctaatcacc aaaactcatc tcagtccgga taaaggctg  caattcgcct  1200
ttttgaagtt ggaatcacta gtaatcccgt gtcagctata tcggggtgaa tacgttccca  1260
ggtcttgtac acaccgcccg tcaaactatg agaggaaggg gcatttgaaa acacattcaa  1320
ttgtgtcaag aatgaaactt c                                            1341
```

<210> SEQ ID NO 8
<211> LENGTH: 1342
<212> TYPE: DNA
<213> ORGANISM: Candidatus Mycoplasma turicensis
<220> FEATURE:
<221> NAME/KEY: misc_feature
<222> LOCATION: (1176)..(1177)
<223> OTHER INFORMATION: N stands for any nucleotide.
<220> FEATURE:
<221> NAME/KEY: misc_feature
<222> LOCATION: (1236)..(1236)
<223> OTHER INFORMATION: N stands for any nucleotide.

<400> SEQUENCE: 8

```
gaactgtcaa aaaggcagtt agcggcgaac gggtgagtaa tacatattta acatgccctc    60
cggaaggaaa tagccgttcg aaagaacgat taatgtccta tagtatcctc catcagacag   120
aaggggatt  taaaggtgaa accgccgga ggattggaat atgtcctatt agctagttgg   180
cgggataaaa gcccaccaag gcgatgatag gtagctggtc taagaggatg aacagccaca   240
atgggattga gatacggccc atattcctac gggaagcagc agtagggaat cttccacaat   300
gggcgaaagc ctgatggagc aatgccatgt gaacgatgaa ggccagacag gtcgtaaagt   360
tcttttagag gggaaaaatt tgatggtacc ctctgaataa gtgacagcaa actatgtgcc   420
```

```
agcagctgcg gtaatacata ggtcgcgagc gttattcgga tttattgggc gtaaagcaag      480
cgcaggcgga tgaataagtt ctgcattaaa agcagctgct taacagttgt ttgtgccgaa      540
tactattcat ctagaatgtg gtaggaagtt ttggaattaa atatggagcg gtggaatgtg      600
tagatatatt taagaacacc agaggcgaag gcgaaaactt aggccattat tgacgcttag      660
gcttgaaagt gtgggtagca aatgggatta gataccccag tagtccacac cgtaaacgat      720
gggtattaga tgtcgggatt tgtgtttcgg cgttgtagct tacgtgttaa ataccccgcc      780
tgggtagtac atatgcaaat atgaaactca aaggaattga cggggacctg aacaagtggt      840
ggaacatgtt gcttaattcg ataatacacg aaaaacctta ccaaggtttg acatcctttg      900
caaagccata gaaatatggt ggaggttatc agagtgacag gtggtgcatg gttgtcgtca      960
gctcgtgtca tgagatgttt ggttaagtcc cgcaacgagc gcaaccctac tctttagttg     1020
attgtctaaa gagactgaac agtaatgtat aggaaggatg ggatcacgtc aaatcatcat     1080
gccccttatg ccttgggccg caaacgtgtt acaatggtga gtacaatgtg tcgcgaacca     1140
gcgatggtaa gctaatcacc aaaactcatc tcagtnngga taaaaggctg caattcgcct     1200
ttttgaagtt ggaatcacta gtaatcccgt gtcagntata tcggggtgaa tacgttccca     1260
ggtcttgtac acaccgcccg tcaaactatg agaggaaggg gcatttgaaa acacattcaa     1320
ttgtgtcaag aatgaaactt ct                                              1342

<210> SEQ ID NO 9
<211> LENGTH: 1442
<212> TYPE: DNA
<213> ORGANISM: Candidatus Mycoplasma turicensis

<400> SEQUENCE: 9
ctatttaggt gacactatag aatactcaag ctatgcatca agcttggtac cgagctcgga       60
tccactagta acggccgcca gtgtgctgga attcgccctt gaactgtcca aaaggcagtt      120
agcggcgaac gggtgagtaa tacatattta acatgccctc cggaaggaaa tagccgttcg      180
aaagaacgat taatgtccta tagtatcctc catcagacag aagggggatt taaaggtgaa      240
aaccgccgga ggattggaat atgtcctatt agctagttgg cgggataaaa gcccaccaag      300
gcgatgatag gtagctggtc taagaggatg aacagccaca atgggattga gatacggccc      360
atattcctac gggaagcagc agtagggaat cctccacaat gggcgaaagc ctgatggagc      420
aatgccatgt gaacgatgaa ggccagacag gtcgtaaagt tcttttagag gggaaaaatt      480
tgatggtacc ctctgaataa gtgacagcaa actatgtgcc agcagctgcg gtaatacata      540
ggtcgcgagc gttattcgga tttattgggc gtaaagcaag cgcaggcgga tgaataagtt      600
ctgcattaaa agcagctgct taacagttgt ttgtgccgaa tactattcat ctagaatgtg      660
gtaggaagtt ttggaattaa atatggagcg gtggaatgtg tagatatatt taagaacacc      720
agaggcgaag gcgaaaactt aggccattat tgacgcttag gcttgaaagt gtgggtagca      780
aatgggatta gataccccag tagtccgcac cgtaaacgat gggtattaga tgtcgggatt      840
tgtgtttcgg cgttgtagct tacgtgttaa ataccccgcc tgggtagtac atatgcaaat      900
atgaaactca aaggaattga cggggacctg aacaagtggt ggaacatgtt gcttaattcg      960
ataatacacg aaaaacctta ccaaggtttg acatcctttg caaagccata gaaatatggt     1020
ggaggttatc agagtgacag gtggtgcatg gttgtcgtca gctcgtgtca tgagatgttt     1080
ggttaagtcc cgcaacgagc gcaaccctac tctttagttg attgtctaaa gagactgaac     1140
```

```
agtaatgtat aggaaggatg ggatcacgtc aaatcatcat gccccttatg ccttgggccg    1200
caaacgtgtt acaatggtga gtacaatgtg tcgcgaacca gcgatggtaa gctaatcacc    1260
aaaactcatc tcagtccgga taaaaggctg caattcgcct ttttgaagtt ggaatcacta    1320
gtaatcccgt gtcagctata tcggggtgaa tacgttccca ggtcttgtac acaccgcccg    1380
tcaaactatg agaggaaggg gcatttgaaa acacattcaa ttgtgtcaag aatgaaactt    1440
ct                                                                  1442

<210> SEQ ID NO 10
<211> LENGTH: 1342
<212> TYPE: DNA
<213> ORGANISM: Candidatus Mycoplasma turicensis

<400> SEQUENCE: 10
gaactgtcca aaaggcagtt agcggcgaac gggtgagtaa tacatattta acatgccctc      60
cggaaggaaa tagccgttcg aaagaacgat taatgtccta tagtatcctc catcagacag     120 aaggggg att taaaggtgaa accgccgga ggattggaat atgtcctatt agctagttgg     180
cgggataaaa gccccaccaag gcgatgatag gtagctggtc taagaggatg aacagccaca     240
atgggattga gatacggccc atattcctgc gggaagcagc agtagggaat cttccacaat     300
gggcgaaagc ctgatggagc aatgccatgt gaacgatgaa ggccagacag gtcgtaaagt     360
tcttttagag gggaaaaatt tgatggtacc ctctgaataa gtgacagcaa gctatgtgcc     420
agcagctgcg gtaatacata ggtcgcgagc gttattcgga tttattgggc gtaaagcaag     480
cgcaggcgga tgaataagtt ctgcattaaa agcagctgct taacagttgt tgtgccgaa     540 tactattcat ctagaatgtg gtaggaagtt ttggaattaa atatggagcg gtggaatgtg     600
tagatatatt taagaacacc agaggcgaag gcgaaaactt aggccattat tgacgcttag     660
gcttgaaagt gtgggtagca aatgggatta gatacccccag tagtccacac cgtaaacgat     720
gggtattaga tgtcgggatt tgtgtttcgg cgttgtagct tacgtgttaa atacccccgcc     780 tgggtagtac atatgcaaat atgaaactca aaggaattga cggggacctg aacaagtggt     840
ggaacatgtt gcttaattcg ataatacacg aaaaacctta ccaaggtttg acatcctttg     900
caaagccata gaaatatggt ggaggttatc agagtgacag gtggtgcatg gttgtcgtca     960
gctcgtgtca tgagatgttt ggttaagtcc cgcaacgagc gcaaccctac tctttagttg    1020
attgtctaaa gagactgaac agtaatgtat aggaaggatg ggatcacgtc aaatcatcat    1080
gccccttatg ccttgggccg caaacgtgtt acaatggtga gtacaatgtg tcgcgaacca    1140
gcgatggtaa gctaatcacc aaaactcatc tcagtccgga taaaaggctg caattcgcct    1200
ttttgaagtt ggaatcacta gtaatcccgt gtcagctata tcggggtgaa tacgttccca    1260
ggtcttgtac acaccgcccg tcaaactatg agaggaaggg gcatttgaaa acacattcaa    1320
ttgtgtcaag aatgaaactt ct                                             1342

<210> SEQ ID NO 11
<211> LENGTH: 1366
<212> TYPE: DNA
<213> ORGANISM: Candidatus Mycoplasma turicensis
<220> FEATURE:
<221> NAME/KEY: misc_feature
<222> LOCATION: (638)..(638)
<223> OTHER INFORMATION: n stands for any nucleotide

<400> SEQUENCE: 11
gaattcgccc ttgaact taacatgccc tccggaagga aatagccgtt cgaaagaacg attaatgtcc tatagtatcc        120
tccatcagac agaaggggga tttaaaggtg aaaaccgccg gaggattgga atatgtccta        180
ttagctagtt ggcgggataa aagcccacca aggcgatgat aggtagctgg tctaagagga        240
tgaacagcca caatgggatt gagatacggc ccatattcct acgggaagca gcagtaggga        300
atcttccaca atgggcgaaa gcctgatgga gcaatgccat gtgaacgatg aaggccagac        360
aggtcgtaaa gttctttttag aggggaaaaa tttgatggta ccctctgaat aagtgacagc        420
aaactatgtg ccagcagctg cggtaataca taggtcgcga gcgttattcg gatttattgg        480
gcgtaaagca agcgcaggcg gatgaataag ttctgcatta aaagcagctg cttaacagtt        540
gtttgtgccg aatactattc atctagaatg tggtaggaag ttttggaatt aaatatggag        600
cggtggaatg tgtagatata tttaagaaca ccagaggnga aggcgaaaac ttaggccatt        660
attgacgctt aggcttgaaa gtgtgggtag caaatgggat tagatacccc agtagtccac        720
accgtaaacg atgggtatta gatgtcggga tttgtgtttc ggcgttgtag cttacgtgtt        780
aaataccccg cctgggtagt acatatgcaa atatgaaact caaaggaatt gatgggacc         840 tgaacaagtg gtggaacatg ttgcttaatt cgataataca cgaaaaacct taccaaggct        900
tgacatcctt tgcaaagcca tagaaatatg gtggaggtta tcagagtgac aggtggtgca        960
tggttgtcgt cagctcgtgt catgagatgt ttggttaagt cccgcaacga gcgcaaccct       1020
actctttagt tgattgtcta aagagactga acagtaatgt ataggaagga tgggatcacg       1080
tcaaatcatc atgccccta tgccttgggc cgcaaacgtg ttacaatggt gagtacaatg        1140
tgtcgcgaac cagcgatggt aagctaatca ccaaaactca tctcagtccg gataaaaggc       1200
tgcaattcgc cttttttgaag ttggaatcac tagtaatccc gtgtcagcta tcggggtg        1260 aatacgttcc caggtcttgt acacaccgcc cgtcaaacta tgagaggaag gggcatttga       1320
aaacacattc aattgtgtca agaatgaaac ttctaagggc gaattc                      1366

<210> SEQ ID NO 12
<211> LENGTH: 1395
<212> TYPE: DNA
<213> ORGANISM: Candidatus Mycoplasma turicensis
<220> FEATURE:
<221> NAME/KEY: misc_feature
<222> LOCATION: (47)..(47)
<223> OTHER INFORMATION: n stands for any nucleotide
<220> FEATURE:
<221> NAME/KEY: misc_feature
<222> LOCATION: (52)..(53)
<223> OTHER INFORMATION: n stands for any nucleotide
<220> FEATURE:
<221> NAME/KEY: misc_feature
<222> LOCATION: (56)..(56)
<223> OTHER INFORMATION: n stands for any nucleotide
<220> FEATURE:
<221> NAME/KEY: misc_feature
<222> LOCATION: (58)..(58)
<223> OTHER INFORMATION: n stands for any nucleotide
<220> FEATURE:
<221> NAME/KEY: misc_feature
<222> LOCATION: (61)..(61)
<223> OTHER INFORMATION: n stands for any nucleotide
<220> FEATURE:
<221> NAME/KEY: misc_feature
<222> LOCATION: (102)..(103)
<223> OTHER INFORMATION: n stands for any nucleotide
<220> FEATURE:
<221> NAME/KEY: misc_feature
<222> LOCATION: (130)..(130)
<223> OTHER INFORMATION: n stands for any nucleotide
<220> FEATURE:

-continued

```
<221> NAME/KEY: misc_feature
<222> LOCATION: (151)..(156)
<223> OTHER INFORMATION: n stands for any nucleotide
<220> FEATURE:
<221> NAME/KEY: misc_feature
<222> LOCATION: (159)..(159)
<223> OTHER INFORMATION: n stands for any nucleotide
<220> FEATURE:
<221> NAME/KEY: misc_feature
<222> LOCATION: (161)..(161)
<223> OTHER INFORMATION: n stands for any nucleotide
<220> FEATURE:
<221> NAME/KEY: misc_feature
<222> LOCATION: (164)..(164)
<223> OTHER INFORMATION: n stands for any nucleotide
<220> FEATURE:
<221> NAME/KEY: misc_feature
<222> LOCATION: (166)..(166)
<223> OTHER INFORMATION: n stands for any nucleotide
<220> FEATURE:
<221> NAME/KEY: misc_feature
<222> LOCATION: (168)..(169)
<223> OTHER INFORMATION: n stands for any nucleotide
<220> FEATURE:
<221> NAME/KEY: misc_feature
<222> LOCATION: (182)..(182)
<223> OTHER INFORMATION: n stands for any nucleotide
<220> FEATURE:
<221> NAME/KEY: misc_feature
<222> LOCATION: (192)..(193)
<223> OTHER INFORMATION: n stands for any nucleotide
<220> FEATURE:
<221> NAME/KEY: misc_feature
<222> LOCATION: (228)..(228)
<223> OTHER INFORMATION: n stands for any nucleotide
<220> FEATURE:
<221> NAME/KEY: misc_feature
<222> LOCATION: (246)..(246)
<223> OTHER INFORMATION: n stands for any nucleotide
<220> FEATURE:
<221> NAME/KEY: misc_feature
<222> LOCATION: (285)..(285)
<223> OTHER INFORMATION: n stands for any nucleotide
<220> FEATURE:
<221> NAME/KEY: misc_feature
<222> LOCATION: (312)..(312)
<223> OTHER INFORMATION: n stands for any nucleotide
<220> FEATURE:
<221> NAME/KEY: misc_feature
<222> LOCATION: (335)..(335)
<223> OTHER INFORMATION: n stands for any nucleotide
<220> FEATURE:
<221> NAME/KEY: misc_feature
<222> LOCATION: (346)..(346)
<223> OTHER INFORMATION: n stands for any nucleotide
<220> FEATURE:
<221> NAME/KEY: misc_feature
<222> LOCATION: (353)..(353)
<223> OTHER INFORMATION: n stands for any nucleotide
<220> FEATURE:
<221> NAME/KEY: misc_feature
<222> LOCATION: (377)..(377)
<223> OTHER INFORMATION: n stands for any nucleotide
<220> FEATURE:
<221> NAME/KEY: misc_feature
<222> LOCATION: (380)..(380)
<223> OTHER INFORMATION: n stands for any nucleotide
<220> FEATURE:
<221> NAME/KEY: misc_feature
<222> LOCATION: (389)..(389)
<223> OTHER INFORMATION: n stands for any nucleotide
<220> FEATURE:
<221> NAME/KEY: misc_feature
<222> LOCATION: (423)..(423)
<223> OTHER INFORMATION: n stands for any nucleotide
<220> FEATURE:
<221> NAME/KEY: misc_feature
<222> LOCATION: (454)..(455)
<223> OTHER INFORMATION: n stands for any nucleotide
```

```
<220> FEATURE:
<221> NAME/KEY: misc_feature
<222> LOCATION: (608)..(608)
<223> OTHER INFORMATION: n stands for any nucleotide
<220> FEATURE:
<221> NAME/KEY: misc_feature
<222> LOCATION: (645)..(645)
<223> OTHER INFORMATION: n stands for any nucleotide
<220> FEATURE:
<221> NAME/KEY: misc_feature
<222> LOCATION: (750)..(750)
<223> OTHER INFORMATION: n stands for any nucleotide
<220> FEATURE:
<221> NAME/KEY: misc_feature
<222> LOCATION: (782)..(782)
<223> OTHER INFORMATION: n stands for any nucleotide
<220> FEATURE:
<221> NAME/KEY: misc_feature
<222> LOCATION: (786)..(787)
<223> OTHER INFORMATION: n stands for any nucleotide
<220> FEATURE:
<221> NAME/KEY: misc_feature
<222> LOCATION: (859)..(859)
<223> OTHER INFORMATION: n stands for any nucleotide
<220> FEATURE:
<221> NAME/KEY: misc_feature
<222> LOCATION: (864)..(864)
<223> OTHER INFORMATION: n stands for any nucleotide
<220> FEATURE:
<221> NAME/KEY: misc_feature
<222> LOCATION: (930)..(930)
<223> OTHER INFORMATION: n stands for any nucleotide
<220> FEATURE:
<221> NAME/KEY: misc_feature
<222> LOCATION: (939)..(939)
<223> OTHER INFORMATION: n stands for any nucleotide
<220> FEATURE:
<221> NAME/KEY: misc_feature
<222> LOCATION: (941)..(941)
<223> OTHER INFORMATION: n stands for any nucleotide
<220> FEATURE:
<221> NAME/KEY: misc_feature
<222> LOCATION: (945)..(945)
<223> OTHER INFORMATION: n stands for any nucleotide
<220> FEATURE:
<221> NAME/KEY: misc_feature
<222> LOCATION: (950)..(950)
<223> OTHER INFORMATION: n stands for any nucleotide
<220> FEATURE:
<221> NAME/KEY: misc_feature
<222> LOCATION: (961)..(961)
<223> OTHER INFORMATION: n stands for any nucleotide
<220> FEATURE:
<221> NAME/KEY: misc_feature
<222> LOCATION: (975)..(975)
<223> OTHER INFORMATION: n stands for any nucleotide
<220> FEATURE:
<221> NAME/KEY: misc_feature
<222> LOCATION: (977)..(977)
<223> OTHER INFORMATION: n stands for any nucleotide
<220> FEATURE:
<221> NAME/KEY: misc_feature
<222> LOCATION: (989)..(989)
<223> OTHER INFORMATION: n stands for any nucleotide
<220> FEATURE:
<221> NAME/KEY: misc_feature
<222> LOCATION: (1063)..(1064)
<223> OTHER INFORMATION: n stands for any nucleotide
<220> FEATURE:
<221> NAME/KEY: misc_feature
<222> LOCATION: (1067)..(1067)
<223> OTHER INFORMATION: n stands for any nucleotide
<220> FEATURE:
<221> NAME/KEY: misc_feature
<222> LOCATION: (1142)..(1142)
<223> OTHER INFORMATION: n stands for any nucleotide
<220> FEATURE:
<221> NAME/KEY: misc_feature
<222> LOCATION: (1161)..(1161)
```

```
<223> OTHER INFORMATION: n stands for any nucleotide
<220> FEATURE:
<221> NAME/KEY: misc_feature
<222> LOCATION: (1175)..(1175)
<223> OTHER INFORMATION: n stands for any nucleotide
<220> FEATURE:
<221> NAME/KEY: misc_feature
<222> LOCATION: (1178)..(1178)
<223> OTHER INFORMATION: n stands for any nucleotide
<220> FEATURE:
<221> NAME/KEY: misc_feature
<222> LOCATION: (1180)..(1180)
<223> OTHER INFORMATION: n stands for any nucleotide
<220> FEATURE:
<221> NAME/KEY: misc_feature
<222> LOCATION: (1181)..(1181)
<223> OTHER INFORMATION: n stands for any nucleotide
<220> FEATURE:
<221> NAME/KEY: misc_feature
<222> LOCATION: (1191)..(1191)
<223> OTHER INFORMATION: n stands for any nucleotide
<220> FEATURE:
<221> NAME/KEY: misc_feature
<222> LOCATION: (1196)..(1196)
<223> OTHER INFORMATION: n stands for any nucleotide
<220> FEATURE:
<221> NAME/KEY: misc_feature
<222> LOCATION: (1203)..(1203)
<223> OTHER INFORMATION: n stands for any nucleotide
<220> FEATURE:
<221> NAME/KEY: misc_feature
<222> LOCATION: (1207)..(1207)
<223> OTHER INFORMATION: n stands for any nucleotide
<220> FEATURE:
<221> NAME/KEY: misc_feature
<222> LOCATION: (1211)..(1211)
<223> OTHER INFORMATION: n stands for any nucleotide
<220> FEATURE:
<221> NAME/KEY: misc_feature
<222> LOCATION: (1343)..(1343)
<223> OTHER INFORMATION: n stands for any nucleotide
<220> FEATURE:
<221> NAME/KEY: misc_feature
<222> LOCATION: (1350)..(1350)
<223> OTHER INFORMATION: n stands for any nucleotide
<220> FEATURE:
<221> NAME/KEY: misc_feature
<222> LOCATION: (1357)..(1357)
<223> OTHER INFORMATION: n stands for any nucleotide
<220> FEATURE:
<221> NAME/KEY: misc_feature
<222> LOCATION: (1361)..(1361)
<223> OTHER INFORMATION: n stands for any nucleotide

<400> SEQUENCE: 12
cagaattaac gctggtggca tgcctaatac atgcaagtcg agcgaantgt cnnaangnca      60
nttagcggcg aacgggtgag taatacatat ttaacatgcc cnncggaagg aaatagccgt     120
tcgaaagaan gattaatgtc ctatagtatc nnnnnncana nagnangnng atttaaaggt     180
gnaaaccgcc gnnggattgg aatatgtcct attagctagt tggcgggnta aaagcccacc     240
aaggcnatga taggtagctg gtctaagagg atgaacagcc acaangggat tgagatacgg     300
cccatattcc tncgggaagc agcagtaggg aatcntccac aatggncgaa agnctgatgg     360
agcaatgcca tgtgaangan gaaggccana caggtcgtaa agttctttta gaggggaaaa     420
atntgatggt accctctgaa taagtgacag caanntatgt gccagcagct gcggtaatac     480
ataggtcgcg agcgttattc ggatttattg ggcgtaaagc aagcgcaggc ggatgaataa     540
gttctgcatt aaaagcagct gcttaacagt tgtttgtgcc gaatactatt catctagaat     600
gtggtagnaa gttttggaat taaatatgga gcggtggaat gtgtngatat atttaagaac     660
accagaggcg aaggcgaaaa cttaggccat tattgacgct taggcttgaa agtgtgggta     720
```

```
gcaaatggga ttagatacccc cagtagtccn caccgtaaac gatgggtatt agatgtcggg    780
anttgnnttt cggcgttgta gcttacgtgt aaatacccc gcctgggtag tacatatgca     840
aatatgaaac tcaaaggant tgangggac ctgaacaagt ggtggaacat gttgcttaat    900
tcgataatac acgaaaaacc ttaccaaggn ttgacatcnt ntgcnaagcn atagaaatat   960
ngtggaggtt atcanantga caggtggtnc atggttgtcg tcagctcgtg tcatgagatg   1020
tttggttaag tcccgcaacg agcgcaaccc tactctttag ttnnttntct aaagagactg   1080
aacagtaatg tataggaagg atgggatcac gtcaaatcat catgccccctt atgccttggg  1140 cngcaaacgt gttacaatgg ngagtacaat gtgtngcnan ncagcgatgg naagcnaatc   1200
acnaaanctc ntctcagtcc ggataaaagg ctgcaattcg ccttttgaa gttggaatca    1260 ctagtaatcc cgtgtcagct atatcggggt gaatacgttc ccaggtcttg tacacaccgc   1320
ccgtcaaact atgagaggaa ggngcatttn aaaacanatt naattgtgtc aagaatgaaa   1380
cttctgattg gagtt                                                    1395

<210> SEQ ID NO 13
<211> LENGTH: 23
<212> TYPE: DNA
<213> ORGANISM: Candidatus Mycoplasma turicensis

<400> SEQUENCE: 13
cgaattgtcg aaagacaatt agc                                           23

<210> SEQ ID NO 14
<211> LENGTH: 27
<212> TYPE: DNA
<213> ORGANISM: Candidatus Mycoplasma turicensis

<400> SEQUENCE: 14
agaagtttca ttcttgacac aatttaa                                       27

<210> SEQ ID NO 15
<211> LENGTH: 1419
<212> TYPE: DNA
<213> ORGANISM: Candidatus Mycoplasma turicensis

<400> SEQUENCE: 15
cagaattaac gctggtggca tgcctaatac atgcaagtcg agcgaattgt cgaaagacaa    60
ttagcggcga acgggtgagt aatacatatt taacatgccc cccggaagga aatagccgtt   120
cgaaagaacg attaatgtcc tatagtatcc cctttcagac agaaaggaga tttaaaggtg   180
caaaccgccg agggattgga atatgtccta ttagctagtt ggcgggataa aagcccacca   240
aggcaatgat aggtagctgg tctaagagga tgaacagcca caatgggatt gagatacggc   300
ccatattcct acgggaagca gcagtaggga atcttccaca atggacgaaa gtctgatgga   360
gcaatgccat gtgaacgacg aaggccagac aggtcgtaaa gttcttttag agggaaaaa    420 tctgatggta ccctctgaat aagtgacagc aaactatgtg ccagcagctg cggtaataca   480
taggtcgcga gcgttattcg gatttattgg gcgtaaagca agcgcaggcg gatgaataag   540
ttctgcatta aaagcagctg cttaacagtt gtttgtgccg aatactattc atctagaatg   600
tggtagaaag ttttggaatt aaatatggag cggtggaatg tgtggatata tttaagaaca   660
ccagaggcga aggcgaaaac ttaggccatt attgacgctt aggcttgaaa gtgtgggtag   720
caaatgggat tagataccccc agtagtccac accgtaaacg atgggtatta gatgtcggga   780
```

| cttgagtttc | ggcgttgtag | cttacgtgtt | aaatacccg | cctgggtagt | acatatgcaa | 840 |
| atatgaaact | caaaggaatt | gacgggacc | tgaacaagtg | gtggaacatg | ttgcttaatt | 900 |
| cgataataca | cgaaaaacct | taccaaggtt | tgacatcctc | tgcaaagcta | tagaaatata | 960 |
| gtggaggtta | tcagagtgac | aggtggtgca | tggttgtcgt | cagctcgtgt | catgagatgt | 1020 |
| ttggttaagt | cccgcaacga | gcgcaaccct | actctttagt | tacttgtcta | aagagactga | 1080 |
| acagtaatgt | ataggaagga | tgggatcacg | tcaaatcatc | atgcccctta | tgccttgggc | 1140 |
| cgcaaacgtg | ttacaatggc | gagtacaatg | tgttgcaaac | cagcgatggt | aagccaatca | 1200 |
| ccaaaactcg | tctcagtccg | gataaaaggc | tgcaattcgc | cttttgaag | ttggaatcac | 1260 |
| tagtaatccc | gtgtcagcta | tatcggggtg | aatacgttcc | caggtcttgt | acacaccgcc | 1320 |
| cgtcaaacta | tgagggaag | gagcatttaa | aaacatatta | aattgtgtca | agaatgaaac | 1380 |
| ttctgattgg | agttaagtcg | taacaaggta | gcggatccg | | | 1419 |

<210> SEQ ID NO 16
<211> LENGTH: 1294
<212> TYPE: DNA
<213> ORGANISM: Candidatus Mycoplasma turicensis

<400> SEQUENCE: 16

| gcggcgaacg | ggtgagtaat | acatatttaa | catgccccc | ggaaggaaat | agccgttcga | 60 |
| aagaacgatt | aatgtcctat | agtatcccct | ttcagacaga | aaggagattt | aaaggtgcaa | 120 |
| accgccgagg | gattgaata | tgtcctatta | gctagttggc | gggataaaag | cccaccaagg | 180 |
| caatgatagg | tagctggtct | aagaggatga | acagccacaa | tgggattgag | atacggccca | 240 |
| tattcctacg | ggaagcagca | gtagggaatc | ttccacaatg | gacgaaagtc | tgatggagca | 300 |
| atgccatgtg | aacgacgaag | gccagacagg | tcgtaaagtt | cttttagagg | ggaaaaatct | 360 |
| gatggtaccc | tctgaataag | tgacagcaaa | ctatgtgcca | gcagctgcgg | taatacatag | 420 |
| gtcgcgagcg | ttattcggat | ttattgggcg | taaagcaagc | gcaggcggat | gaataagttc | 480 |
| tgcattaaaa | gcagctgctt | aacagttgtt | tgtgccgaat | actattcatc | tagaatgtgg | 540 |
| tagaaagttt | tggaattaaa | tatggagcgg | tggaatgtgt | agatatattt | aagaacacca | 600 |
| gaggcgaagg | cgaaaactta | ggccattatt | gacgcttagg | cttgaaagtg | tgggtagcaa | 660 |
| atgggattag | atacccccagt | agtccacacc | gtaaacgatg | gtattagat | gtcgggactt | 720 |
| gagtttcggc | gttgtagctt | acgtgttaaa | taccccgcct | gggtagtaca | tatgcaaata | 780 |
| tgaaactcaa | aggaattgac | ggggacctga | acaagtggtg | gaacatgttg | cttaattcga | 840 |
| taatacacga | aaaaccttac | caaggtttga | catcctctgc | aaagctatag | aaatatagtg | 900 |
| gaggttatca | gagtgacagg | tggtgcatgg | ttgtcgtcag | ctcgtgtcat | gagatgtttg | 960 |
| gttaagtccc | gcaacgagcg | caaccctact | ctttagttac | ttgtctaaag | agactgaaca | 1020 |
| gtaatgtata | ggaaggatgg | gatcacgtca | atcatcatg | cccttatgc | cttgggccgc | 1080 |
| aaacgtgtta | caatggcgag | tacaatgtgt | tgcaaccag | cgatggtaag | ccaatcacca | 1140 |
| aaactcgtct | cagtccggat | aaaaggctgc | aattcgcctt | tttgaagttg | gaatcactag | 1200 |
| taatcccgtg | tcagctatat | cggggtgaat | acgttcccag | gtcttgtaca | caccgcccgt | 1260 |
| caaactatga | gaggaaggag | catttaaaaa | cata | | | 1294 |

<210> SEQ ID NO 17
<211> LENGTH: 1294
<212> TYPE: DNA
<213> ORGANISM: Candidatus Mycoplasma turicensis

<400> SEQUENCE: 17

```
gcggcgaacg ggtgagtaat acatatttaa catgcccccc ggaaggaaat agccgttcga      60
aagaacgatt aatgtcctat agtatcccct ttcagacaga aaggagattt aaaggtgcaa     120
accgccgagg gattggaata tgtcctatta gctagttggc gggataaaag cccaccaagg     180
caatgatagg tagctggtct aagaggatga acagccacaa tgggattgag atacggccca     240
tattcctacg ggaagcagca gtagggaatc ttccacaatg gacgaaagtc tgatggagca     300
atgccatgtg aacgacgaag ccagacagg tcgtaaagtt cttttagagg ggaaaaatct      360
gatggtaccc tctgaataag tgacagcaaa ctatgtgcca gcagctgcgg taatacatag     420
gtcgcgagcg ttattcggat ttattgggcg taaagcaagc gcaggcggat gaataagttc     480
tgcattaaaa gcagctgctt aacagttgtt tgtgccgaat actattcatc tagaatgtgg     540
tagaaagttt tggaattaaa tatggagcgg tggaatgtgt agatatattt aagaacacca     600
gaggcgaagg cgaaaactta ggccattatt gacgcttagg cttgaaagtg tgggtagcaa     660
atgggattag atacccccagt agtccacacc gtaaacgatg gtattagat gtcgggactt      720
gagtttcggc gttgtagctt acgtgttaaa taccccgcct gggtagtaca tatgcaaata     780
tgaaactcaa aggaattgac ggggacctga acaagtggtg gaacatgttg cttaattcga     840
taatacacga aaaccttac caaggtttga catcctctgc aaagctatag aaatatagtg      900
gaggttatca gagtgacagg tggtgcatgg ttgtcgtcag ctcgtgtcat gagatgtttg     960
gttaagtccc gcaacgagcg caaccctact ctttagttac ttgtctaaag agactgaaca    1020
gtaatgtata ggaaggatgg gatcacgtca atcatcatg ccccttatgc cttgggccgc     1080
aaacgtgtta caatggcgag tacaatgtgt tgcaaaccag cgatggtaag ccaatcacca    1140
aaactcgtct cagtccggat aaaaggctgc aattcgcctt tttgaagttg gaatcactag    1200
taatcccgtg tcagctatat cggggtgaat acgttcccag gtcttgtaca caccgcccgt    1260
caaactatga gaggaaggag catttaaaaa cata                                1294
```

<210> SEQ ID NO 18
<211> LENGTH: 1341
<212> TYPE: DNA
<213> ORGANISM: Candidatus Mycoplasma turicensis

<400> SEQUENCE: 18

```
gaactgtcca aaaggcagtt agcggcgaac gggtgagtaa tacatatttta acatgcccta     60
cggaaggaaa tagccgttcg aaagaacgat taatgtccta tagtatcctc cctcagacag    120
aaggggggatt taaaggtgaa aaccgccgaa ggattggaat atgtcctatt agctagttgg    180
cgggataaaa gcccaccaag gcaatgatag gtagctggtc taagaggatg aacagccaca    240
acggattga gatacggccc atattcctac gggaagcagc agtagggaat cttccacaat      300
gggcgaaagc ctgatggagc aatgccatgt gaatgatgaa ggccagacag gtcgtaaagt    360
tcttttagag gggaaaaatc tgatggtacc ctctgaataa gtgacagcaa actatgtgcc    420
agcagctgcg gtaatacata ggtcgcgagc gttattcgga tttattgggc gtaaagcaag    480
cgcaggcgga tgaataagtt ctgcattaaa gcagctgct taacagttgt tgtgccgaa      540
tactattcat ctagaatgtg gtaggaagtt ttggaattaa atatggagcg gtggaatgtg    600
tagatatatt taagaacacc agaggcgaag gcgaaaactt aggccattat tgacgcttag    660
gcttgaaagt gtgggtagca atgggattga gatacccag tagtccacac cgtaaacgat      720
```

```
gggtattaga tgtcgggatt tgtgtttcgg cgttgtagct tacgtgttaa atacccccgcc      780 tgggtagtac atatgcaaat atgaaactca aggaattga cggggacctg aacaagtggt        840
ggaacatgtt gcttaattcg ataatacacg aaaaaccta ccaaggtttg acatcctttg        900
caaagccata gaaatatggt ggaggttatc agagtgacag gtggtgcatg gttgtcgtca      960
gctcgtgtca tgagatgttt ggttaagtcc cgcaacgagc gcaaccctac tctttagttg      1020
cttttctaaa gagactgaac agtaatgtat aggaaggatg ggatcacgtc aaatcatcat      1080 gcccccttatg ccttgggccg caaacgtgtt acaatggtga gtacaatgtg tcgcaaccca     1140
gcgatggcaa gctaatcact aaagctcatc tcagtccgga taaaaggctg caattcgcct      1200
ttttgaagtt ggaatcacta gtaatcccgt gtcagctata tcggggtgaa tacgttccca      1260
ggtcttgtac acaccgcccg tcaaactatg agaggaaggg gcatttgaaa acacattcaa      1320
ttgtgtcaag aatgaaactt c                                                 1341
```

<210> SEQ ID NO 19
<211> LENGTH: 1343
<212> TYPE: DNA
<213> ORGANISM: Candidatus Mycoplasma turicensis

<400> SEQUENCE: 19

```
ttgaactgtc caaaaggcag ttagcggcga acgggtgagt aatacatatt taacatgccc      60
ttcggaagga aatagccgtt cgaaagaatg attaatgtcc tatagtatct ttccccaaaa      120
ggaggaagat ttaaaggtga aaaccgccga aggattggaa tatgtcctat tagctagttg      180
gcggggtaaa agcccaccaa ggcgatgata ggtagctggt ctaagaggat gaacagccac      240
aatgggattg atacggcc catattccta cgggaagcag cagtagggaa tcttccacaa        300
tgggcgaaag cctgatggag caatgccatg tgaacgatga aggccaaaca ggtcgtaaag      360
ttcttttaga ggggaaaaat ctgatggtac cctctgaata agtgacagca aactatgtgc      420
cagcagctgc ggtaatacat aggtcgcgag cgttattcgg atttattggg cgtaaagcaa      480
gcgcaggcgg atgaataagt tctgcattaa aagcagctgc ttaacagttg tttgtgccga      540
atactattca tctagaatgt ggtagaaagt tttggaatta aatatggagc ggtgaatgt       600 gtagatatat ttaagaacac cagaggcgaa ggcgaaaact taggccatta ttgacgctta     660
ggcttgaaag tgtgggtagc aaatgggatt agatacccca gtagtccaca ccgtaaacga     720
tgggtattag atgtcgggat ttgaatttcg gcgttgtagc ttacgtgtta aatacccccgc    780 ctgggtagta catatgcaaa tatgaaactc aaaggaattg acggggacct gaacaagtgg     840
tggaacatgt tgcttaattc gataatacac gaaaaacctt accaaggttt gacatcttt     900 gcgaagctat agaaatatag tggaggttat caaaatgaca ggtggtacat ggttgtcgtc     960
agctcgtgtc atgagatgtt tggttaagtc ccgcaacgag cgcaacccta ctctttagtt     1020
atttgtctaa agagactgaa cagtaatgta taggaaggat gggatcacgt caaatcatca     1080 tgcccccttat gccttgggct gcaaacgtgt tacaatggcg agtacaatgt gtcgcaaatc     1140
agcgatggta agctaatcac taaaactcgt ctcagtccgg ataaaaggct gcaattcgcc     1200 ttttttgaagt tggaatcact agtaatcccg tgtcagctat atcggggtga atacgttccc     1260
aggtcttgta cacaccgccc gtcaaactat gagaggaagg gcatttaaa aacacattca     1320 attgtgtcaa gaatgaaact tct                                              1343
```

FELINE HEMOPLASMA ISOLATE

PRIORITY

This application claims the benefit of U.S. Provisional Application No. 60/677,383, filed May 3, 2005. The provisional application is hereby incorporated by reference herein in its entirety, including the drawings.

BACKGROUND OF THE INVENTION

Recently, there has been a growing interest in hemotropic mycoplamal species (also known as the hemoplasmas), the causative agents of infectious anemia in several mammalian species. In felids, two different hemoplasma species have been recognized: *Mycoplasma haemofelis* (formerly *Haemobartonella felis*) and 'Candidatus *Mycoplasma haemominutum*.'

*Haemobartonella felis*, the causative agent of feline infectious anemia, was recently reclassified within a newly defined group of hemotropic mycoplasmal species (also known as the hemoplasmas). Sequencing of the 16S ribosomal RNA (rRNA) gene of different feline isolates has resulted in the recognition of two different species (Berent et al. 1998. Am J Vet Res 59:1215-20; Foley et al. 1998. Am J Vet Res 59:1581-8; Messick et al. 1998. J Clin Microbiol 36:462-6; Rikihisa et al. 1997. J Clin Microbiol 35:823-9; Tasker et al., 2003. J Clin Microbiol 41:3877-80), *Mycoplasma haemofelis* and 'Candidatus *Mycoplasma haemominutum*' (Johansson et al. 1999. FEMS Microbiol Lett 174:321-6; Neimark et al. 2001. Int J Syst Evol Microbiol 51:891-9; Rikihisa et al. 1997 J. Clin. Microbiol. 35:823-829), that parasitize feline red blood cells (RBC) (Messick et al. 1998. J Clin Microbiol 36:462-6). Experimental infection studies have shown that the two species differ in pathogenicity (Foley et al. 1998. Am J. Vet Res 59:1581-1588; Tasker et al. 2003. J Clin Microbiol 41:3877-80; Westfall et al. 2001. Am J Vet Res 62:687-91): cats experimentally infected with 'Candidatus *M. haemominutum*' exhibit minimal clinical signs and anemia is not usually induced whilst *M. haemofelis* infection often results in severe hemolytic anemia. Since *M. haemofelis* and 'Candidatus *M. haemominutum*' cannot be cultured in vitro, diagnosis until recently has relied upon cytological identification on blood smears (Bobade et al. 1987. Vet Parasitol 26:169-72). However, the development of new molecular methods has facilitated the sensitive and specific identification and quantification of these agents (Berent et al. 1998. Am J Vet Res 59:1215-1220; Jensen et al. 2001. Am J Vet Res 62:604-8; Tasker et al. 2003. J Clin Microbiol 41:3877-80), and PCR analysis is now the diagnostic method of choice for identification of hemoplasma infections. There is still little knowledge of the epidemiology of these agents. Both species have been shown to exhibit worldwide geographical distribution (Clark et al. 2002. Aust Vet J 80:703-4; Criado-Fomelio et al. 2003. Vet Microbiol 93:307-17; Jensen et al. 2001. Am J Vet Res 62:604-8; Tasker et al. 2001. Vet Microbiol 81:73-8; Tasker et al. 2003. J Clin Microbiol 41:3877-80; Watanabe et al. 2003. J Vet Med Sci 65:1111-4) and isolates from three different continents have shown near sequence identities (Tasker et al. 2003. J Clin Microbiol 41:3877-80). We now unexpectedly identified a third hemoplasma agent, "Candidatus *Mycoplasma turicensis*," which has been deposited with ATCC under the Budapest Treaty as PTA-6782.

SUMMARY OF THE INVENTION

One embodiment of the invention provides an isolated hemoplasma agent, wherein a polymerase chain reaction (PCR) performed using nucleic acids of the hemoplasma agent with PCR primers consisting of SEQ ID NO:1 and SEQ ID NO:2; or SEQ ID NO:3 and SEQ ID NO:4; or SEQ ID NO:13 and SEQ ID NO:14; results in an amplification product. The amplification product amplified by SEQ ID NO:1 and SEQ ID NO:2 can be about 1342 nucleic acids in length; the amplification product amplified by SEQ ID NO:3 and SEQ ID NO:4 can be about 85 nucleotides in length; and the amplification product amplified by SEQ ID NO:13 and SEQ ID NO:14 can be about 1342 nucleic acids in length. The hemoplasma agent can comprise a 16S rRNA sequence of SEQ ID NO:12.

Another embodiment of the invention provides an isolated nucleic acid molecule comprising SEQ ID NO:12, or a nucleic acid molecule comprising 10 or more contiguous nucleic acids of SEQ ID NO:12. The isolated nucleic acid molecule can comprise SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19; 10 or more contiguous nucleic acids of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11; SEQ ID NO:12, SEQ ID NO:13, SEQ ID NO:14, SEQ ID NO:15, SEQ ID NO:16, SEQ ID NO:17, SEQ ID NO:18, SEQ ID NO:19; or combinations thereof. The isolated nucleic acid molecule can comprise a label.

Even another embodiment of the invention comprises a method of detecting the presence or absence of a hemoplasma agent of the invention in a sample. The method comprises contacting the sample with an isolated nucleic acid probe comprising SEQ ID NO:12 or 10 or more contiguous nucleic acids of SEQ ID NO:12; and detecting the presence or absence of hybridized probe/hemoplasma agent nucleic acid complexes, wherein the presence of hybridized probe/hemoplasma agent nucleic acid complexes indicates the presence of the hemoplasma agent in the sample. The quantity of hybridized probe/hemoplasma agent nucleic acid complexes can be determined. The probe can comprise a label, which can be a fluorescent moiety.

Still another embodiment of the invention provides a method for detecting the presence or absence of a hemoplasma agent of the invention in a subject. The method comprises detecting 16S rRNA of the hemoplasma agent, or a nucleic acid molecule encoding the 16S rRNA in a sample obtained from the subject, wherein the presence of 16S rRNA or a nucleic acid molecule encoding the 16S rRNA indicates the presence of the hemoplasma agent. The detecting can comprise amplifying a 16S rRNA nucleic acid molecule of the hemoplasma agent by a method selected from the group consisting of, e.g., polymerase chain reaction (PCR); ligase chain reaction; nucleic acid sequence-based amplification; self-sustained sequence replication; strand displacement amplification; branched DNA signal amplification; nested PCR; multiplex PCR; quantitative PCR; direct detection, in situ hybridization; Transcription Mediated Amplification (TMA); Rolling Circle Amplification (RCA); and Q-beta-replicase system. The detecting can comprise use of an isolated nucleic acid probe comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19; 10 or more contiguous nucleic acids of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11; SEQ ID NO:12, SEQ ID NO:13, SEQ ID NO:14, SEQ ID NO:15, SEQ ID NO:16, SEQ ID NO:17, SEQ ID NO:18, SEQ ID NO:19; or combinations thereof.

Yet another method of the invention provides a method of detecting 16S rRNA nucleic acid molecules of a hemoplasma agent of the invention in a sample. The method comprises amplifying 16S rRNA nucleic acid molecules of the hemoplasma agent using a first amplification primer consisting of SEQ ID NO:1 or SEQ ID NO:3 or SEQ ID NO:13, and a second amplification primer consisting of SEQ ID NO:2 or SEQ ID NO:4 or SEQ ID NO:14; and detecting an amplification product, wherein if an amplification product is detected, the 16S rRNA nucleic acid molecule is present. The quantity of the 16S rRNA nucleic acid molecules in the sample can be determined. The first or second or both amplification primers can further comprise a label, such as a fluorescent moiety. The amplifying can comprise real-time quantitative PCR and further comprises using a DNA polymerase with 5' nuclease activity and at least one probe comprising a detectable label. The at least one probe can consist of SEQ ID NO:6. The amplifying can comprise real-time quantitative PCR and can further comprise using a detectable dye that binds to double-stranded DNA. The detectable dye can be, e.g., syber-green or ethidium bromide.

Another embodiment of the invention provides a method for detecting and quantifying nucleic acid molecules of a hemoplasma agent of the invention. The method comprises amplifying a 16S rRNA sequence of the hemoplasma agent using a first primer consisting of SEQ ID NO:1 or SEQ ID NO:3 or SEQ ID NO:13; a second primer consisting of SEQ ID NO:2 or SEQ ID NO:4, SEQ ID NO:14; a DNA polymerase comprising 5' nuclease activity; a nucleic acid probe comprising nucleic acids complementary to the 16S rRNA sequence and comprising a reporter fluorescent dye and a quencher dye; wherein the nucleic acid from the hemoplasma agent is detected and quantified.

Even another embodiment of the invention provides a kit for detecting a nucleic acid molecule. The kit comprises one or more isolated nucleic acid molecules having a sequence comprising SEQ ID NO:12; ten or more contiguous nucleic acids of SEQ ID NO:12, or combinations thereof. The kit can further comprise a polymerase and one or more buffers. The one or more isolated nucleic acid molecules comprise one or more labels. The label is a fluorescent moiety.

Yet another embodiment of the invention provides a method of isolating hemoplasma agent 16S rRNA nucleic acid molecules from a sample. The method comprises contacting a solid support comprising one or more isolated capture nucleic acids, wherein the isolated capture nucleic acids comprise SEQ ID NO:12 or 10 or more contiguous nucleic acids of SEQ ID NO:12, with the sample under hybridizing conditions wherein the hemoplasma agent 16S rRNA nucleic acid molecules, if present in the sample, hybridize with the capture nucleic acids; and detecting the hybridized hemoplasma agent 16S rRNA nucleic acid molecules on the solid support.

Still another embodiment of the invention provides a method for monitoring the efficacy of a treatment of a subject infected with a hemoplasma agent of the invention. The method comprises obtaining a pre-treatment sample from the subject; detecting the presence, absence, amount, or combination thereof of hemoplasma 16S rRNA nucleic acid molecules in the sample; obtaining one or more post-treatment samples from the subject; detecting the presence, absence, or combination thereof of a hemoplasma 16S rRNA nucleic acid in the post-treatment samples; comparing the presence, absence, amount, or combination thereof of 16S rRNA nucleic acid in the pre-administration sample with the that of the post-administration sample; and monitoring the efficacy of treatment.

Another embodiment of the invention provides a method for screening a subject for an infection with a hemoplasma agent of the invention. The method comprises detecting a polynucleotide comprising SEQ ID NO:12 or 10 or more contiguous nucleic acids of SEQ ID NO:12 in a sample obtained from the subject, wherein if the polynucleotide is detected, then the subject has an infection with the hemoplasma agent.

Even another embodiment of the invention provides a method for screening a subject for an infection with a hemoplasma agent of the invention. The method comprises detecting a polynucleotide comprising SEQ ID NO:12 or 10 or more contiguous nucleic acids of SEQ ID NO:12 in a sample obtained from the subject to provide a first value; detecting a polynucleotide comprising SEQ ID NO:12 or 10 or more contiguous nucleic acids of SEQ ID NO:12 in a similar biological sample obtained from a disease-free subject to provide a second value; and comparing the first value with the second value, wherein a greater first value relative to the second value is indicative of the subject having an infection with the hemoplasma agent.

DETAILED DECRIPTION OF THE INVENTION

Hemoplasma Agent

Figure 1:
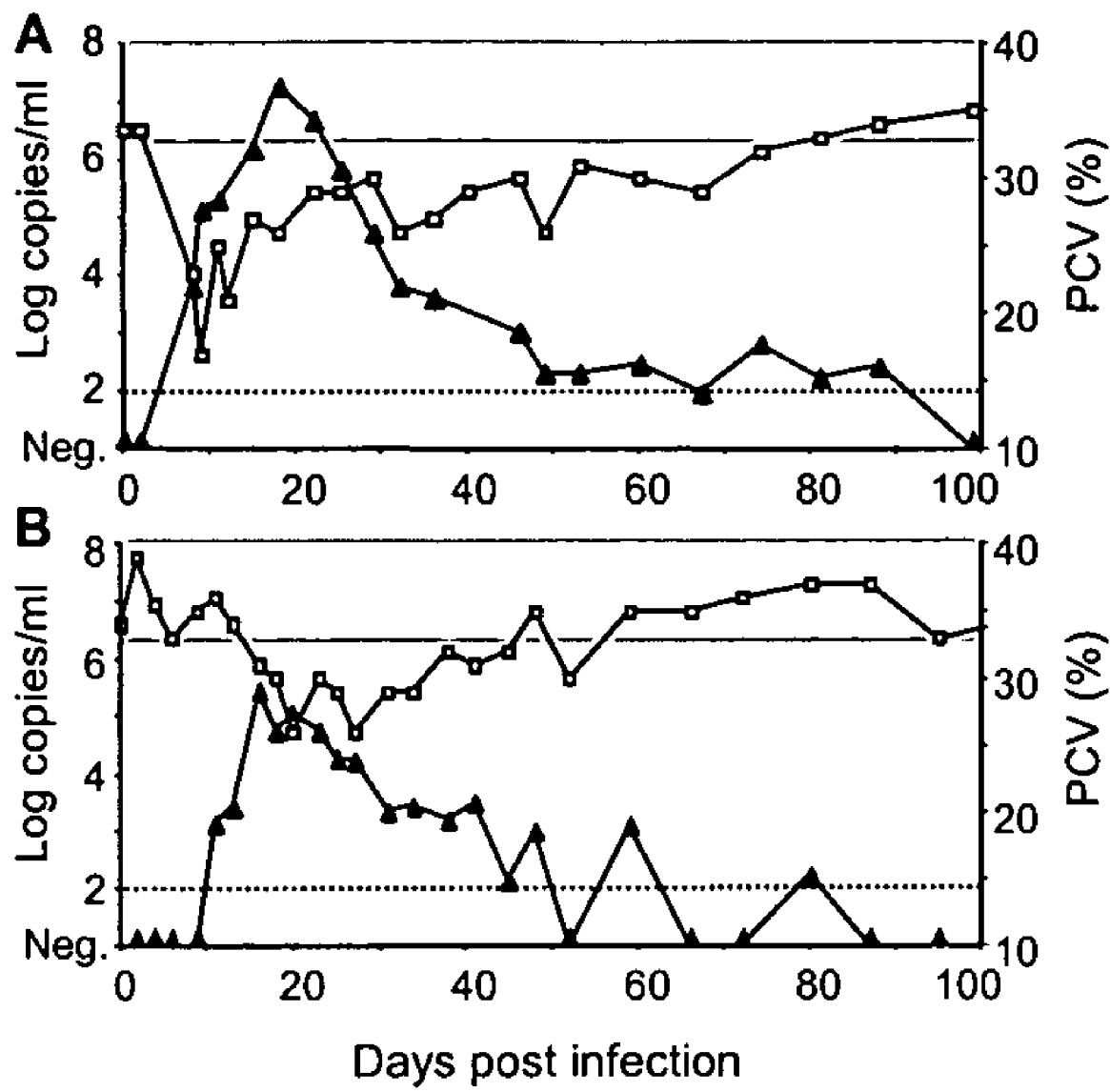
FIG. 1 shows a transmission experiment. The load of the newly described isolate (log copy number of DNA template per ml of blood, left y-axis, black triangles) and course of packed cell volume (PCV) (%, right y-axis, open squares) in Cat 1 (A) and Cat 2 (B) over 100 days p.i. The reference range of PCV is shaded grey. The lower detection limit of the real-time PCR assay (100 copies/ml blood) is indicated by a dotted line.

Recently developed molecular methods have allowed sensitive and specific identification and quantification of hemoplasma agents in feline blood samples. In applying these methods to an epidemiological study surveying the Swiss pet cat population for hemoplasma infection, a third novel and unique feline hemoplasma isolate was identified, 'Candidatus *Mycoplasma turicensis*,' which was deposited under the Budapest Treaty on Jun. 8, 2005 as PTA-6782.

The new isolate was discovered in a blood sample collected from a cat that had exhibited clinical signs of severe hemolytic anemia. The agent was readily transmitted via intravenous inoculation to two specific pathogen free cats. One of these cats (Cat 1) was immunocompromised by administering methylprednisolone acetate prior to inoculation and this cat developed severe anemia. The other immunocompetent cat (Cat 2) showed a moderate decrease in packed cell volume. Additionally, an increase in erythrocyte osmotic fragility was observed. Sequencing of the entire 16S rRNA gene of the new hemoplasma isolate, and phylogenetic analysis, showed that the new isolate was most closely related to two rodent hemotropic mycoplasmal species, *M. coccoides* and *M. haemomuris*. A quantitative real-time PCR assay specific for this newly discovered agent was developed.

The new hemoplasma isolate was originally identified in a naturally infected cat (Cat 946) that had exhibited clinical signs of haemobartonellosis. Clinical and laboratory examination of the naturally infected cat revealed signs of severe intravascular hemolysis, with a minimal PCV of 12%. The newly discovered agent induced severe anemia (to a PCV of 17%) by day 9 p.i. in an experimentally infected, immunocompromised cat (Cat 1). The cat had been immunocompromised using methylprednisolone acetate. This corticosteroid alone is not known to cause a decrease in PCV and, in fact, has been used in the treatment of cats with aplastic anemia and immune-mediated hemolytic anemia due to its ability to increase the half-life of RBC by decreasing their removal by the spleen (Plumb. 1995. Veterinary Drug Handbook. $2^{nd}$ ed. Ames, Iowa: Iowa State University Press:325-328, 443-446). The immunocompromised cat developed only mild clinical signs, indicating that additional environmental factors could have been involved in the development of severe illness observed in the naturally infected cat. Although different susceptibilities of individual cats to feline hemoplasmas have been observed in larger experimental transmission studies, it is still unknown which specific factors influence the severity and clinical outcome of infection.

The hemoplasma loads in Cat 1 and Cat 2 (a non-immunocompromised cat) were inversely correlated with PCV. A non-immunocompromised cat (Cat 2) experimentally infected with the new hemoplasma isolate developed only mild anemia and no signs of clinical illness. This complies with the fact that clearly lower hemoplasma loads were measured in the blood of this cat compared to the immunocompromised cat (Cat 1), and further strengthens the presumption that additional factors are involved in the development of acute illness caused by this agent.

Feline hemoplasmas, especially *Mycoplasma haemofelis*, are known to induce acute hemolysis in infected cats, although the exact mechanism underlying the RBC destruction is still unknown. Maede et al. (1975. Nippon Juigaku Zasshi 37:49-54) claimed a central role of the spleen in sequestrating parasitized erythrocytes and removing attached organisms from the erythrocyte cell surface. They reported a marked and continuous increase in RBC osmotic fragility following the first appearance of hemoplasma species on the RBC surfaces of experimentally infected cats. An increased RBC osmotic fragility was also observed in this study for all three cats naturally or experimentally infected with the new hemoplasma isolate. As reported for the non-immunocompromised cat (Cat 2), the RBC osmotic fragility increased continuously during the first month p.i., before returning to normal values. Nevertheless, the most pronounced increase in osmotic fragility was measured in the naturally infected cat (Cat 946), consistent with the fact that this cat developed the most severe degree of anemia and signs of intravascular hemolysis.

*M. haemofelis* and 'Candidatus *M. haemominutum*' show worldwide geographical distribution. Since the development of conventional and quantitative real-time PCR assays to detect and differentiate these two feline hemoplasma agents in blood samples, both species have been identified in cats from the USA (Jensen et al. 2001. Am J Vet Res 62:604-8), UK (Tasker et al. 2001. Vet Microbiol 81:73-8), Spain (Criado-Fomelio et al. 2003. Vet Microbiol 93:307-17), Japan (Watanabe et al. 2003. J Vet Med Sci 65:1111-4), South Africa (Lobetti & Tasker, 2004, J S Afr Vet Assoc 75:94-99), France, and Australia (Tasker et al. 2003. J Clin Microbiol 41:3877-80).

Phylogenetic analysis of a 16S rRNA gene of a novel hemoplasma isolate of the invention revealed its close relationship to the pathogenic feline hemoplasma isolate *M. haemofelis*, whereas it was only distantly related with the less pathogenic species 'Candidatus *M. haemominutum*'. Surprisingly, a 16S rRNA sequence of the new isolate was even more closely related to *M. coccoides*, a hemoplasma species isolated from rodents. *M coccoides* is known to induce hemolytic anemia in mice and rats with numerous studies demonstrating its pathogenicity (Cox et al. 1976. Ann Trop Med Parasitol 70:73-9; Iralu et al. 1983. Infect Immun 39:963-5; Schilling, 1928. Parasitology 44:81-98). *M. coccoides* has been shown to be mechanically transmitted between mice through the mouse louse *Polyplax serrata* (Berkenkamp et al. 1998. Lab Anim Sci 38:398-401). Experimental transmission of feline hemoplasma species between cats by oral inoculation of infected blood has been successful (Flint et al. 1959. Am J Vet Res 20:33-40). In view of permanent outdoor access and successful mousing reported for Cat 946, one could speculate that, if this new hemoplasma isolate is present in wild rodents in Switzerland, an interspecies transmission from mouse to cat could have taken place through hunting.

In a recent study performed in Swiss pet cats 6 out of 615 feline blood samples tested positive when analyzed by a PCR assay specific for the newly described hemoplasma agent (Willi et al., 2006, J. Clin. Microbiol. 44:961-969).

A sample comprising hemoplasma agents of the invention comprise those that when a PCR is performed using nucleic acids of the agent with PCR primers consisting of SEQ ID NO:3 and SEQ ID NO:4 an amplification product is produced. The amplification product can be about 85 nucleic acids in length. Additionally, novel hemoplasma agents of the invention comprise those that when a PCR is performed using a sample comprising nucleic acids of the agent with PCR primers consisting of SEQ ID NO:1 and SEQ ID NO:2 or SEQ ID NO:13 and SEQ ID NO:14 an amplification product is produced. The amplification product can be about 1342 nucleic acids in length for each of these amplifications. A sequence of a 16S rRNA nucleic acid of the novel hemoplasma agents can comprise, for example, SEQ ID NO:5; SEQ ID NO:7; SEQ ID NO:8; SEQ ID NO:9; SEQ ID NO:10; SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19.

Polynucleotides

Nucleic acid molecules of the invention comprise isolated nucleic acid molecules comprising SEQ ID NO:1, SEQ ID NO:2, SEQ ID NO:3, SEQ ID NO:4, SEQ ID NO:5 SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, fragments thereof, or a combinations thereof.

Nucleic acid molecules of the invention can be naturally occurring nucleic acid molecules or recombinant nucleic acid molecules. A nucleic acid molecule also includes amplified products of itself, for example, as in a polymerase chain reaction. A nucleic acid molecule can be a fragment of a hemoplasma 16S rRNA nucleic acid or a whole hemoplasma 16S rRNA nucleic acid. Polynucleotides of the invention can be about 5, 10, 20, 30, 40, 50, 100, 200, 300, 400, 500, 600, 700, 800, 900, 1,000, 1,200, 1,300 or more nucleic acids in length. A polynucleotide fragment of the invention can comprise about 5, 10, 20, 30, 40, 50, 100, 200, 300, 400, 500, 600, 700, 800, 900, 1,000, 1,200, 1,300 or more contiguous nucleic acids of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19. A nucleic acid molecule can be RNA, or DNA encoding the RNA, and can contain a modified nucleotide or nucleotide analog.

A nucleic acid, nucleic acid molecule, polynucleotide or polynucleotide molecule refers to covalently linked sequences of nucleotides (i.e., ribonucleotides for RNA and deoxyribonucleotides for DNA) in which the 3' position of the pentose of one nucleotide is joined by a phosphodiester group to the 5' position of the pentose of the next. A polynucleotide can be RNA, DNA, cDNA, genomic DNA, chemically synthesized RNA or DNA, or combinations thereof. A nucleic acid molecule can comprises chemically, enzymatically or metabolically modified forms of nucleic acids.

Nucleic acid molecules of the invention can also include, for example, polydeoxyribonucleotides (containing 2-deoxy-D-ribose), polyribonucleotides (containing D-ribose), any other type of polynucleotide which is an N- or C-glycoside of a purine or pyrimidine base, and other polymers containing normucleotidic backbones, for example, polyamide (e.g., peptide nucleic acids (PNAs)) and polymorpholino polymers, and other synthetic sequence-specific nucleic acid polymers providing that the polymers contain nucleobases in a configuration which allows for base pairing and base stacking, such as is found in DNA and RNA. Nucleic acid molecules also include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates), with negatively charged linkages (e.g., phosphorothioates, phosphorodithioates), and with positively charged linkages (e.g., aminoalkylphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. A nucleotide analog refers to a nucleotide in which the pentose sugar and/or one or more of the phosphate esters is replaced with its respective analog.

The polynucleotides can be purified free of other components, such as proteins, lipids and other polynucleotides. For example, the polynucleotide can be 50%, 75%, 90%, 95%, 96%, 97%, 98%, 99%, or 100% purified. Polynucleotides of the invention can comprise other nucleotide sequences, such as sequences coding for labels, linkers, signal sequences, TMR stop transfer sequences, transmembrane domains, or ligands useful in protein purification such as glutathione-S-transferase, histidine tag, and staphylococcal protein A.

Polynucleotides of the invention contain less than an entire microbial genome. Polynucleotides of the invention can be isolated. An isolated polynucleotide is a polynucleotide that is not immediately contiguous with one or both of the 5' and 3' flanking genomic sequences that it is naturally associated with. An isolated polynucleotide can be, for example, a recombinant DNA or RNA molecule of any length, provided that the nucleic acid sequences naturally found immediately flanking the recombinant DNA or RNA molecule in a naturally-occurring genome is removed or absent. Isolated polynucleotides can be naturally-occurring or non-naturally occurring nucleic acid molecules. A nucleic acid molecule existing among hundreds to millions of other nucleic acid molecules within, for example, cDNA or genomic libraries, or gel slices containing a genomic DNA restriction digest are not to be considered an isolated polynucleotide.

Polynucleotides of the invention can comprise naturally occurring 16S rRNA sequences or can comprise altered sequences that do not occur in nature. If desired, polynucleotides can be cloned into an expression vector comprising expression control elements, including for example, origins of replication, promoters, enhancers, or other regulatory elements that drive expression of the polynucleotides of the invention in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

Methods for preparing polynucleotides operably linked to an expression control sequence and expressing them in a host cell are well-known in the art. See, e.g., U.S. Pat. No. 4,366,246. A polynucleotide of the invention is operably linked when it is positioned adjacent to or close to one or more expression control elements, which direct transcription and/or translation of the polynucleotide.

Substantially homologous nucleotide sequences and complements thereof are also polynucleotides of the invention. Homology refers to the percent similarity between two polynucleotides. Two polynucleotide sequences are "substantially homologous" to each other when the sequences exhibit at least about 95%, 98%, 99%, 99.5% or 100% sequence similarity over a defined length of the molecules. As used herein, substantially homologous also refers to sequences showing complete identity to the specified polynucleotide sequence.

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomput-*

*ing: Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al., *Nuc. Acids Res.* 12:387 (1984)), BLASTP, BLASTN, FASTA (Atschul et al., *J. Molec. Biol.* 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (*Adv. App. Math.*, 2:482-489 (1981)). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polynucleotide and that gaps in identity of up to 5% of the total number of nucleotides in the reference polynucleotide are allowed.

Polynucleotides of the invention can be isolated from nucleic acid sequences present in, for example, a biological sample, such as blood, serum, saliva, or tissue from an infected individual. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides of the invention can be used, for example, as probes or primers, for example PCR primers, to detect hemoplasma agent polynucleotides in a sample, such as a biological sample. The ability of such probes and primers to specifically hybridize to hemoplasma agent polynucleotide molecules will enable them to be of use in detecting the presence, absence and/or quantity of complementary nucleic acid molecules in a given sample. Polynucleotide probes and primers of the invention can hybridize to complementary sequences in a sample such as a biological sample. Polynucleotides from the sample can be, for example, subjected to gel electrophoresis or other size separation techniques or can be immobilized without size separation. The polynucleotides from the sample are contacted with the probes or primers under hybridization conditions of suitable stringencies.

A probe is a nucleic acid molecule of the invention comprising a sequence that has complementarity to a hemoplasma agent nucleic acid molecule of the invention and that can hybridize to the hemoplasma agent nucleic acid molecule.

A primer is a nucleic acid molecule of the invention that can hybridize to a hemoplasma agent nucleic acid molecule through base pairing so as to initiate an elongation (extension) reaction to incorporate a nucleotide into the nucleic acid primer. Preferably, the elongation reactions occur in the presence of nucleotides and a polymerization-inducing agent such as a DNA or RNA polymerase and at suitable temperature, pH, metal concentration, and salt concentration.

Polynucleotide hybridization involves providing denatured polynucleotides (e.g., a probe or primer or combination thereof and hemoplasma nucleic acid molecules) under conditions where the two complementary (or partially complementary) polynucleotides form stable hybrid duplexes through complementary base pairing. The polynucleotides that do not form hybrid duplexes can be washed away leaving the hybridized polynucleotides to be detected, e.g., through detection of a detectable label. Alternatively, the hybridization can be performed in a homogenous reaction in which all reagents are present at the same time and no washing is involved.

Hybridization and the strength of hybridization (i.e., the strength of the association between polynucleotide strands) is impacted by many factors well known in the art including the degree of complementarity between the polynucleotides, stringency of the hybridization conditions, e.g., conditions as the concentration of salts, the thermal melting temperature (Tm) of the formed hybrid, the presence of other components (e.g., the presence or absence of polyethylene glycol), the molarity of the hybridizing strands and the G:C content of the polynucleotide strands. Tm is the temperature at which 50% of a population of double-stranded polynucleotide molecules becomes dissociated into single strands.

Under high stringency conditions, polynucleotide pairing will occur only between polynucleotide molecules that have a high frequency of complementary base sequences. Thus, conditions of "weak" or "low" stringency are often required when it is desired that polynucleotides that are not completely complementary to one another be hybridized or annealed together. Generally, high stringent conditions can include a temperature of about 5 to 20 degrees C. lower than the Tm of a specific nucleic acid molecule at a defined ionic strength and pH. An example of high stringency conditions comprises a washing procedure including the incubation of two or more hybridized polynucleotides in an aqueous solution containing 0.1×SSC and 0.2% SDS, at room temperature for 2-60 minutes, followed by incubation in a solution containing 0.1× SSC at room temperature for 2-60 minutes. An example of low stringency conditions comprises a washing procedure including the incubation of two or more hybridized polynucleotides in an aqueous solution comprising 1×SSC and 0.2% SDS at room temperature for 2-60 minutes. Stringency conditions are known to those of skill in the art, and can be found in, for example, Maniatis et al., 1982, Molecular Cloning, Cold Spring Harbor Laboratory.

In one embodiment, a polynucleotide molecule of the invention comprises one or more labels. A label is a molecule capable of generating a detectable signal, either by itself or through the interaction with another label. A label can be a directly detectable label or can be part of a signal generating system, and thus can generate a detectable signal in context with other parts of the signal generating system, e.g., a biotin-avidin signal generation system, or a donor-acceptor pair for fluorescent resonance energy transfer (FRET). The label can, for example, be isotopic or non-isotopic, a catalyst, such as an enzyme, a polynucleotide coding for a catalyst, promoter, dye, fluorescent molecule, chemiluminescer, coenzyme, enzyme substrate, radioactive group, a small organic molecule, amplifiable polynucleotide sequence, a particle such as latex or carbon particle, metal sol, crystallite, liposome, cell, a colorimetric label, catalyst or other detectable group. A label can be a member of a pair of interactive labels. The members of a pair of interactive labels interact and generate a detectable signal when brought in close proximity. The signals can be detectable by visual examination methods well known in the art, preferably by FRET assay. The members of a pair of interactive labels can be, for example, a donor and an acceptor, or a receptor and a quencher.

Detection and Quantification

A sample includes, for example, purified nucleic acids, unpurified nucleic acids, cells, cellular extract, tissue, organ fluid, bodily fluid, tissue sections, specimens, aspirates, bone marrow aspirates, tissue biopsies, tissue swabs, fine needle aspirates, skin biopsies, blood, serum, lymph fluid, cerebrospinal fluid, seminal fluid, stools, or urine.

Detection and quantification of a hemoplasma agent or hemoplasma agent nucleic acid of the invention can be done using any method known in the art, including, for example, direct sequencing, hybridization with probes, gel electrophoresis, transcription mediated amplification (TMA) (e.g., U.S. Pat. No. 5,399,491), polymerase chain reaction (PCR,) quantitative PCR, replicase mediated amplification, ligase chain reaction (LCR), competitive quantitative PCR (QPCR), real-time quantitative PCR, self-sustained sequence replication, strand displacement amplification, branched DNA signal amplification, nested PCR, in situ hybridization, multiplex PCR, Rolling Circle Amplification (RCA), Q-beta-replicase system, and mass spectrometry. These methods can use heterogeneous or homogeneous formats, and labels or no labels, and can detect or detect and quantify.

Nucleic acid-based detection techniques allow identification of hemoplasma target nucleic acid sequences in samples. The methods are particularly useful for detecting hemoplasma nucleic acids in blood samples, including without limitation, in whole blood, serum and plasma. The methods can be used to diagnose hemoplasma agent infection in a subject, such as a mammal, including, for example, a human, cat or rodent.

Hemoplasma agent target nucleic acids can be separated from non-homologous nucleic acids using capture polynucleotides immobilized, for example, on a solid support. The capture oligonucleotides can be derived from hemoplasma agents of the invention and are specific for hemoplasma agents of the invention. The separated target nucleic acids can then be detected, for example, by the use of polynucleotide probes, also derived from hemoplasma agents of the invention. More than one probe can be used. Particularly useful capture polynucleotides comprise SEQ ID NOs:1-19 or fragments thereof comprising 10 or more contiguous nucleic acids of SEQ ID NOs1-19.

In one embodiment of the invention a sample is contacted with a solid support in association with capture polynucleotides. The capture polynucleotides can be associated with the solid support by, for example, covalent binding of the capture polynucleotide to the solid support, by affinity association, hydrogen binding, or nonspecific association.

A capture polynucleotide can be immobilized to the solid support using any method known in the art. For example, the polynucleotide can be immobilized to the solid support by attachment of the 3' or 5' terminal nucleotide of the probe to the solid support. Alternatively, the capture polynucleotide can be immobilized to the solid support by a linker. A wide variety of linkers are known in the art that can be used to attach the polynucleotide probe to the solid support. The linker can be formed of any compound that does not significantly interfere with the hybridization of the target sequence to the capture polynucleotide associated with the solid support.

A solid support can be, for example, particulate nitrocellulose, nitrocellulose, materials impregnated with magnetic particles or the like, beads or particles, polystyrene beads, controlled pore glass, glass plates, polystyrene, avidin-coated polystyrene beads, cellulose, nylon, acrylamide gel and activated dextran.

The solid support with immobilized capture polynucleotides is brought into contact with a sample under hybridizing conditions. The capture polynucleotides hybridize to the target polynucleotides present in the sample.

The solid support can then be separated from the sample, for example, by filtering, washing, passing through a column, or by magnetic means, depending on the type of solid support. The separation of the solid support from the sample preferably removes at least about 70%, more preferably about 90% and, most preferably, at least about 95% or more of the non-target nucleic acids and other debris present in the sample.

A hemoplasma agent or hemoplasma nucleic acid of the invention can also be detected and quantified using, for example, an amplification reaction such as quantitative PCR, such as transcription mediated amplification, polymerase chain reaction (PCR) (Innis et al. (eds.) PCR Protocols (Academic Press, NY 1990); Taylor (1991) Polymerase chain reaction: basic principles and automation, in PCR: A Practical Approach, McPherson et al. (eds.) IRL Press, Oxford; Saiki et al. (1986) Nature 324:163; U.S. Pat. Nos. 4,683,195, 4,683, 202 and 4,889,818), replicase mediated amplification, ligase chain reaction (LCR), competitive quantitative PCR (QPCR), relative quantitative PCR, and real-time quantitative PCR (e.g., the fluorogenic 5' nuclease assay, known as the TAQ-MAN® assay; Holland et al., Proc. Natl. Acad. Sci. USA (1991) 88:7276-7280; see also, Higuchi et al., Biotechnology (NY). 1993 September;11(9):1026-30). These methods can be semi-quantitative or fully quantitative.

An internal control (IC) or an internal standard can be added to an amplification reaction serve as a control for target capture and amplification. Preferably, the IC includes a sequence that differs from the target sequences, is capable of hybridizing with the capture polynucleotides used for separating the nucleic acids specific for the hemoplasma agent from the sample, and is capable of amplification by the primers used to amplify the hemoplasma agent nucleic acids.

In one embodiment of the invention the sequence of the hemoplasma agent 16S rRNA can be used to detect the presence or absence of the hemoplasma agent of in a sample. For example, a sample can be contacted with a probe comprising SEQ ID NOs:1-19 or a probe comprising 10 or more contiguous nucleic acids of SEQ ID NOs:1-19. The probe can comprise a label, such as a fluorescent label. The presence or absence of hybridized nucleic acid probe/hemoplasma agent nucleic acid complexes is detected. The presence of hybridized probe/hemoplasma agent nucleic acid complexes indicates the presence of a hemoplasma agent of the invention in the sample. The quantity of hybridized nucleic acid probe/hemoplasma agent nucleic acid complexes can be determined.

Another embodiment of the invention provides a method of detecting a 16S rRNA nucleic acid molecule of a hemoplasma agent of the invention in a sample. 16S rRNA nucleic acid molecules of the hemoplasma agent are amplified using a first amplification primer comprising SEQ ID NO:1 or SEQ ID NO:3 or SEQ ID NO:13 and a second amplification primer comprising SEQ ID NO:2 or SEQ ID NO:4 or SEQ ID NO:14. The amplified hemoplasma agent 16S rRNA nucleic acid molecules are detected using any methodology known in the art. Amplification products can be assayed in a variety of ways, including size analysis, restriction digestion followed by size analysis, detecting specific tagged oligonucleotide primers in the reaction products, allele-specific oligonucleotide (ASO) hybridization, sequencing, and the like. The quantity of the amplified hemoplasma agent 16S rRNA nucleic acid molecules can also be determined. The first or second or both amplification primers can further comprise a label, such as a fluorescent moiety. The amplifying method can be real-time quantitative PCR and can further comprise using a DNA polymerase with 5' nuclease activity and at least one probe, for example SEQ ID NO:6, comprising a label.

Alternatively, the amplifying method can comprise real-time quantitative PCR and can further comprise using a detectable dye that binds to double-stranded DNA, such as syber-green or ethidium bromide.

Another embodiment of the invention provides a method for detecting and quantifying a nucleic acid from a hemoplasma agent of the invention. The method comprises amplifying a 16S rRNA sequence of the hemoplasma agent using a first primer comprising SEQ ID NO:1 or SEQ ID NO:3 or SEQ ID NO:13; a second primer comprising SEQ ID NO:2 or SEQ ID NO:4 or SEQ ID NO:14; a DNA polymerase comprising 5' nuclease activity; a nucleic acid probe comprising nucleic acids complementary to the 16S rRNA sequence and comprising a reporter fluorescent dye and a quencher dye.

Another embodiment of the invention provides a method for detecting a hemoplasma agent of the invention in a sample. A quantitative real-time PCR reaction can be performed with reagents comprising nucleic acid molecules of the hemoplasma agent, a dual-fluorescently labeled nucleic acid hybridization probe, and a set or sets of species-specific primers comprising SEQ ID NO:1 and SEQ ID NO:2, SEQ ID NO:3 and SEQ ID NO:4, and SEQ ID NO:13 and SEQ ID NO:14, or combinations thereof (i.e., one forward and one reverse primer). The fluorescent labels can be detected and read during the PCR reaction. The dual-fluorescently labeled probe can be labeled with a reporter fluorescent dye and a quencher fluorescent dye.

Another method of the invention provides a method of isolating a hemoplasma agent 16S rRNA nucleic acid molecule from a sample. The method comprises contacting a solid support comprising one or more capture nucleic acids, wherein the capture nucleic acids comprise SEQ ID NOs:1-19 or 10 or more contiguous nucleic acids of SEQ ID NOs:1-19 with the sample under hybridizing conditions wherein the hemoplasma agent 16S rRNA nucleic acid molecules, if present in the sample, hybridize with the capture nucleic acids.

Other embodiments of the invention include the protein sequence encoded by SEQ ID NOs:1-19 and fragments of the protein sequences, e.g., amino acid fragments of 6, 10, 20, 30, 50, 100, 150, or more amino acids.

Diagnosis and Monitoring Efficacy of Treatment

Other embodiments of the invention provide methods of diagnosis of infection with a hemoplasma agent of the invention and methods of monitoring the efficacy of treatment of a hemoplasma agent infection. For example, the invention provides a method for monitoring the efficacy of a treatment of a subject having a hemoplasma agent infection. The method comprises obtaining a pre-treatment sample from the subject; detecting the presence, absence, amount, or combination thereof of a hemoplasma 16S rRNA nucleic acid in the sample; obtaining one or more post-treatment samples from the subject; detecting the presence, absence, or combination thereof of a hemoplasma 16S rRNA nucleic acid in the post-treatment samples; comparing the presence, absence, amount, or combination thereof of 16S rRNA nucleic acid in the pre-administration sample with that of the post-administration sample; and determining the efficacy of treatment.

Another embodiment of the invention provides methods for screening a subject for an infection with a hemoplasma agent. A polynucleotide comprising SEQ ID NOs:1-19 or 10 or more contiguous nucleic acids of SEQ ID NOs:1-19 can be detected in a sample obtained from a subject. If the polynucleotide is detected, then the subject has an infection with a hemoplasma agent of the invention. Alternatively, a polynucleotide comprising SEQ ID NOs:1-19 or 10 or more contiguous nucleic acids of SEQ ID NOs:1-19 can be detected in a sample obtained from the subject to provide a first value. A polynucleotide comprising SEQ ID NOs:1-19 or 10 or more contiguous nucleic acids of SEQ ID NOs:1-19 can be detected in a similar biological sample obtained from a disease-free subject to provide a second value. The first value can be compared with the second value, wherein a greater first value relative to the second value is indicative of the subject having an infection with the hemoplasma agent.

Kits

The above-described assay reagents, including primers, probes, solid supports, as well as other detection reagents, can be provided in kits, with suitable instructions and other necessary reagents, in order to conduct, for example, the assays as described above. A kit can contain, in separate containers, the combination of primers and probes (either already bound to a solid support or separate with reagents for binding them to the support), control formulations (positive and/or negative), labeled reagents and signal generating reagents (e.g., enzyme substrate) if the label does not generate a signal directly. Instructions (e.g., written, tape, VCR, CD-ROM) for carrying out the assay can also be included in the kit. The kit can also contain, depending on the particular assay used, other packaged reagents and materials (i.e., wash buffers and the like). Standard assays, such as those described above, can be conducted using these kits.

A kit can comprise, for example, one or more nucleic acid molecules having a sequence comprising SEQ ID NO:1, SEQ ID NO:2, SEQ ID NO:3, SEQ. ID NO:4, SEQ ID NO:5, SEQ ID NO:6; SEQ ID NO:7; SEQ ID NO:8; SEQ ID NO:9; SEQ ID NO:10; SEQ ID NO:11; SEQ ID NO:12, SEQ ID NO:13, SEQ ID NO:14, SEQ ID NO:15, SEQ ID NO:16, SEQ ID NO:17, SEQ ID NO:18, SEQ ID NO:19; ten or more contiguous nucleic acids of SEQ ID NOs:1-19 or combinations thereof, and a polymerase and one or more buffers. The one or more nucleic acid molecules can comprise one or more labels or tags. The label can be a fluorescent moiety.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, without changing the ordinary meanings of these terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The following are provided for exemplification purposes only and are not intended to limit the scope of the invention described in broad terms above. All references cited in this disclosure are incorporated herein by reference.

EXAMPLES

Example 1

Animals and Experimental Design of the Transmission Experiment

A new hemoplasma isolate was discovered in Cat 946, a 13-year-old male castrated cat, which was presented to the Clinic for Small Animal Internal Medicine at the University of Zurich in December 2002. During an epidemiological study to assess the prevalence of M. haemofelis and 'Candidatus M. haemominutum' infection in Swiss cats, Cat 946 was noticeable because of discrepant PCR results. DNA extracted from a blood sample from this cat collected in March 2003 tested positive by means of conventional PCR (Jensen et al.) but negative using a previously published real-time PCR assay specific for M. haemofelis and 'Candidatus M. haemominutum' (Tasker et al. 2003. J Clin Microbiol 41:439-41). The amplified PCR products and, subsequently, the 16S rRNA gene were sequenced and compared to published sequences of other hemoplasma species (see below). Four months prior to presentation, Cat 946 had exhibited clinical signs consistent with haemobartonellosis including lethargy, anorexia, pallor, dyspnoe and weight loss. Examination of blood and urine samples collected at that time revealed signs of intravascular hemolysis with a PCV of 12% (reference value: 33%-45%), leucocytosis ($25.6 \times 10^9$/l; reference value: $5\text{-}18.9 \times 10^9$/l), bilirubinemia (34 µmol/l; reference value: 0-15 µmol/l) and hemoglobinuria. The anemia became high regenerative 4 days after first presentation (PCV 17%; aggregated reticulocyte counts of 201,670/µl with regeneration defined by a count of >60,000/µl). Before the detection of the new hemoplasma isolate in the blood of Cat 946, a primary immune-mediated hemolytic anemia had been suspected and the cat had been treated with corticosteroids. However, this treatment had only resulted in a transient improvement in the cat's clinical status. After diagnosis of a hemoplasma infection, and after blood had been collected for the transmission experiment, Cat 946 was treated with doxycycline (10 mg/kg/d for 14 days). After the initiation of doxycycline treatment, the cat's clinical condition improved. However, RBC osmotic fragility was still increased >1 year after acute illness (50% hemolysis in 0.71% NaCl) (reference range: 50% hemolysis in 0.50%-0.57% NaCl).

To gain first insight into the agent's pathogenic potential, the new hemoplasma isolate was transmitted via intravenous inoculation to Cats 1 and 2. Cat 1 was immunocompromised two weeks prior to inoculation. The blood sample used to inoculate Cat 1 tested negative for FeLV, FIV, FCoV and FPV infection by PCR. The 4 ml inoculum contained $2.8 \times 10^3$ copies of the new hemoplasma isolate as determined by real-time PCR assay. Cat 1 became PCR positive 8 days p.i. and remained positive for 88 days (FIG. 1). It developed anemia, with a drop in PCV from 34% to 17% by 9 days p.i. (FIG. 1). Mild clinical signs of pallor and lethargy were observed. The cat recovered from clinical signs without treatment. However, the PCV remained below the reference range until day 80 p.i. (FIG. 1). The hemoplasma load in Cat 1 was inversely correlated with PCV (rs=0.79; p<0.0001). A maximal load of $1.9 \times 10^7$ copies/ml blood was reached 18 days p.i. (FIG. 1).

Figure 2:
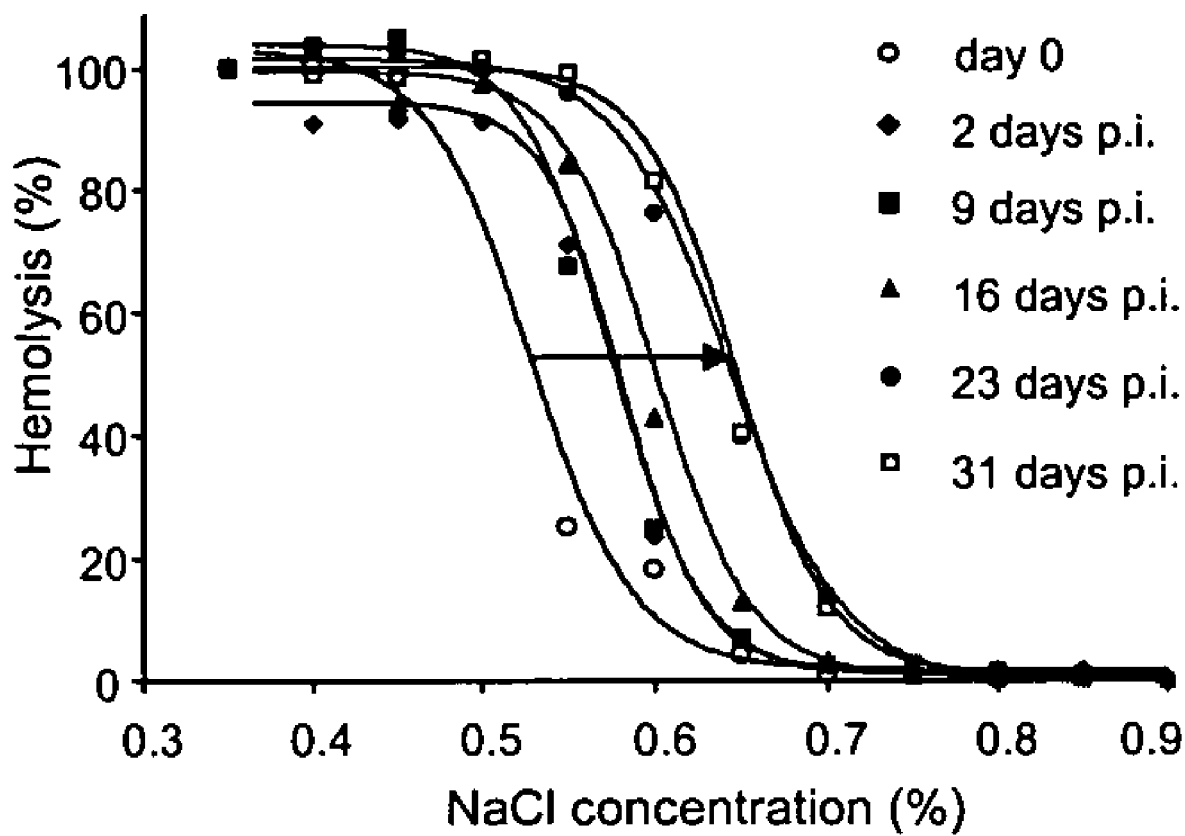
FIG. 2 shows the course of RBC osmotic fragility in Cat 2 over 31 days after experimental infection with the newly described isolate. Percentage (%) of hemolysis was calculated as described in Example 1. The shift of RBC osmotic fragility from days 0 to 31 p.i. is indicated by an arrow.

Cat 2 was inoculated with 4 ml of blood freshly collected from Cat 1 at day 35 p.i., which contained a total of $1.7 \times 10^4$ copies of the new hemoplasma isolate. Cat 2 became PCR positive 7 days p.i. and stayed positive for over 80 days (FIG. 1). This cat developed only a mild anemia with a drop in PCV from 34% to 26% by 27 days p.i. (FIG. 1). Clinical signs of intravascular hemolysis were not observed. Again, the hemoplasma load was inversely correlated with PCV (rs=-0.65; p=0.0002). The hemoplasma load of Cat 2 was lower than that of Cat 1 (p=0.0085; values of 15 time points were compared) and reached a maximum of $2.8 \times 10^5$ copies/ml blood 16 days p.i. (FIG. 1). The RBC osmotic fragility continuously increased (50% hemolysis in 0.52% to 0.64% NaCl) over the first 31 days p.i. (FIG. 2) and returned to normal values on 59 days p.i. (50% hemolysis in 0.54% NaCl).

For the transmission experiment, two specific pathogen free (SPF) cats, designated Cat 1 and Cat 2 (both castrated males, 10 years of age) were used. Both cats were confirmed to be free from infections with the new isolate, M. haemofelis and 'Candidatus M. haemominutum' by means of specific real-time PCR assays (Tasker et al. 2003. J Clin Microbiol 41:439-41). The cats were isolated from any external source of infection. No fresh blood was available from Cat 946 during the acute phase of illness, but fresh heparinized blood was available 10 months later and 4 ml of this blood was used to inoculate Cat 1 intravenously. To increase the probability of successful experimental transmission of the agent, Cat 1 had been immunocompromised by twice administering methylprednisolone acetate (10 mg/kg, IM) two weeks and one week prior to inoculation. Experimental transmission to Cat 2 was performed by intravenous inoculation of 4 ml of heparinized blood freshly collected from Cat 1 at day 35 post infection (p.i.). The blood types of all three cats were tested for compatibility for the transmission experiment prior to inoculation using the RapidVet™-H feline test (Medical Solution Gmbh, Steinhausen, Switzerland). Blood samples from Cats 1 and 2 were collected regularly for 14 weeks (for exact time points see FIG. 1). Additionally, the cats were monitored daily for assessment of body temperature, heart rate, mucous membrane color, attitude and appetite.

Example 2

Hematology and Biochemistry

Complete hemograms were performed from Cat 946, Cat 1, and Cat 2 using an electronic cell counter (Cell-Dyn 3500, Abbott, Baar, Switzerland). Blood smears were made using fresh EDTA-anticoagulated blood and were Giemsa-stained using an AMES Hema Tek slide strainer (Bayer, Zürich, Switzerland). They were evaluated for white blood cell differentials, erythrocyte morphologic characteristics and the presence of hemoplasma organisms. Aggregate reticulocytes were counted after supravital staining with methylene blue. Serum biochemistry was performed on Cat 946 using an automated chemistry analyzer (Cobas Integra 700, Roche Diagnostics, Rotkreuz, Switzerland) by standard procedures recommended by the International Federation of Clinical Chemistry, as reported elsewhere (Tieze. 1995. Clinical guide to laboratory tests, $3^{rd}$ ed. The W.B. Saunders Company, Philadelphia, Pa.). Reference values were determined in the Clinical Laboratory, University of Zurich, Switzerland by identical methods with blood samples from 58 healthy adult cats. Reference ranges are given as the range between the 5% and 95% quantiles.

Example 3

Osmotic Fragility

Osmotic fragility was measured by adding 50 μl of freshly collected EDTA-anticoagulated blood to 5 ml of NaCl solution in concentrations ranging from 0.3 to 0.9%. The contents were mixed gently and incubated at 37° C. for one hour. The tubes were centrifuged at 600×g for 10 minutes. The hemoglobin content of the supernatant fluid was determined spectrophotometrically at 546 nm. A 0.9% NaCl solution was used as a blank. The percentage hemolysis was calculated as follows: absorbance measured in the supernatant after incubation in 0.3% NaCl solution was defined as 100% hemolysis whilst absorbance measured in the supernatant after incubation in 0.9% NaCl solution was defined as 0% hemolysis. Curves were fitted to the data using sigmoid regression (SigmaPlot Regression Wizard, SSPS, Chicago, USA). Osmotic fragility was measured in all blood samples collected from Cat 2 and in selected samples from Cats 1 and 946. Reference values were determined by performing this methodology on blood samples collected from healthy cats (6 SPF and 3 privately owned). Reference ranges are given as the range between the 5% and 95% quantiles.

Example 4

DNA Extraction and Diagnostic PCR Assays

For PCR analysis and sequencing, genomic DNA was purified from 200 μl EDTA-anticoagulated blood using MagNaPure® LC DNA Isolation Kit I (Roche Diagnostics). To monitor for cross-contamination, negative controls consisting of 200 μl of sterile water were concurrently prepared with each batch of samples. Previously published conventional PCR (Jensen et al. 2001 Am J Vet Res 62:604-608) and real-time PCR assays (Tasker et al. 2003. J Clin Microbiol 41:439-41) were performed to detect *M. haemofelis* and 'Candidatus *M. haemominutum*' infections. PCR assays for the detection of feline corona virus (FCoV), feline immunodeficiency virus (FIV), feline leukemia virus (FeLV) and feline parvovirus (FPV) were performed as reported (Foley et al. 1998. Am J Vet Res 59:1581-8; Hofmann-Lehmann 2001. Journal of General Virology 82:1589-1596; Leutenegger 1999. Journal of Virological Methods 78:105-116; Meli et al. 2004. J Feline Med Surg 6:69-81).

Example 5

Sequencing of the 16S rRNA Gene of the New Isolate

Amplification and sequencing of the whole 16S rRNA gene of the new hemoplasma isolate from the blood of Cat 1 was carried out using the previously described universal primers fHf1 and rHf2 (Messick et al. 1998. J Clin Microbiol 36:462-6) in a reaction mixture containing 2.5 μl of 10×PCR buffer (Sigma-Aldrich, Buchs, Switzerland), 800 nM of each primer, 200 μM each of dNTP (Sigma-Aldrich), 2.5 mM $MgSO_4$ and 0.8 Pfu DNA Polymerase (Promega Corporation, Catalys AG, Wallisellen, Switzerland), and 5 μl template DNA, made up to a final volume of 25 μl with water. The thermal program comprised of 51 to 61° C. for 30 s, 72° C. for 3 min, and final elongation of 72° C. for 10 min. Amplified products of the appropriate size (1440 bp) were identified by ethidium bromide staining on a ½% agarose gel, purified with MinElute® Gel Extraction Kit (Quiagen, Hombrechtikon, Switzerland) and then cloned using the Zero Blunt® TOPO® PCR cloning Kit (Invitrogen, Basel, Switzerland) as directed by the manufacturer. As a result of the lower hemoplasma load in Cats 2 and 946, Ampli Taq Gold® DNA Polymerase (Applied Biosystems, Rotkreuz, Switzerland) and species specific primers (forward: 5'-GAA CTG TCC AAA AGG CAG TTA GC-3' (SEQ ID NO:1); reverse: 5'-AGA AGT TTC ATT CTT GAC ACA ATT GAA-3') (SEQ ID NO:2) were used to amplify a 1342 bp product of the 16S rRNA gene of the isolate. The reaction mixture contained 2.5 μl of 10×PCR buffer (Applied Biosystems), 800 nM of each primer, 200 μM each dNTP (Sigma-Aldrich), 1.5 mM $MgCl_2$ and 1.25 U Ampli Taq Gold® DNA Polymerase (Applied Biosystems) and 5 μl of template DNA, made up to a final volume of 25 μl with water. The thermal program comprised one cycle at 95° C. for 5 min, 35 cycles of 95° C. for 30 s, an annealing gradient of 51 to 61° C. for 30 s, 72° C. for 2 min, and final elongation of 72° C. for 10 min. Amplified PCR products were cloned using TOPO TA Cloning® Kit (Invitrogen) as directed by the manufacturer. Grown plasmid DNA was purified using QIAprep® Spin Miniprep Kit (Quiagen) and sequenced using M13 forward and M13 reverse primers. Sequencing of the central region of the 16S rRNA gene was completed using an internal primer (5'-GAA GGC CAG ACA GGT CGT AAA G-3')(SEQ ID NO:3). Sequencing was performed using the BigDye® Cycle Sequencing Ready Reaction Kit (Applied Biosystems). Cycling conditions were as follows: 96° C. for 1 min, 25 cycles at 96° C. for 10 s, 50° C. for 5 s and 60° C. for 4 min. The products were purified with DyeEx® Spin columns (Qiagen) and analyzed on an ABI PRISM® 310 Genetic Analyzer (Applied Biosystems).

The nucleotide sequence of the 16 S rRNA gene of the new isolate (from Cat 946) is shown in SEQ ID NO:5 and has been submitted to GenBank and given the accession number AY831867.

```
                                                                    SEQ ID NO:5
  1 cagaattaac gctggtggca tgcctaatac atgcaagtcg agcgaactgt ccaaaaggca 61 gttagcggcg aacgggtgag taatacatat ttaacatgcc ctccggaagg aaatagccgt 121 tcgaaagaac gattaatgtc ctatagtatc ctccatcaga cagaagggg  atttaaaggt 181 gaaaaccgcc ggaggattgg aatatgtcct attagctagt tggcgggata aaagcccacc 241 aaggcgatga taggtagctg gtctaagagg atgaacagcc acaatgggat tgagatacgg 301 cccatattcc tacgggaagc agcagtaggg aatcttccac aatgggcgaa agcctgatgg 361 agcaatgcca tgtgaacgat gaaggccaga caggtcgtaa agttcttta  gaggggaaaa 421 atttgatggt accctctgaa taagtgacag caaactatgt gccagcagct gcggtaatac
```

```
 481 ataggtcgcg agcgttattc ggatttattg ggcgtaaagc aagcgcaggc ggatgaataa 541 gttctgcatt aaaagcagct gcttaacagt tgtttgtgcc gaatactatt catctagaat 601 gtggtaggaa gttttggaat taaatatgga gcggtggaat gtgtagatat atttaagaac 661 accagaggcg aaggcgaaaa cttaggccat tattgacgct taggcttgaa agtgtgggta 721 gcaaatggga ttagataccc cagtagtcca caccgtaaac gatgggtatt agatgtcggg 781 atttgtgttt cggcgttgta gcttacgtgt taaataccccc gcctgggtag tacatatgca 841 aatatgaaac tcaaaggaat tgacggggac ctgaacaagt ggtggaacat gttgcttaat 901 tcgataatac acgaaaaacc ttaccaaggt ttgacatcct ttgcaaagcc atagaaatat 961 ggtggaggtt atcagagtga caggtggtgc atggttgtcg tcagctcgtg tcatgagatg 1021 tttggttaag tcccgcaacg agcgcaaccc tactctttag ttgattgtct aaagagactg 1081 aacagtaatg tataggaagg atgggatcac gtcaaatcat catgccccctt atgccttggg 1141 ccgcaaacgt gttacaatgg tgagtacaat gtgtcgcgaa ccagcgatgg taagctaatc 1201 accaaaactc atctcagtcc ggataaaagg ctgcaattcg ccttttttgaa gttggaatca 1261 ctagtaatcc cgtgtcagct atatcggggt gaatacgttc ccaggtcttg tacacaccgc 1321 ccgtcaaact atgagaggaa ggggcatttg aaaacacatt caattgtgtc aagaatgaaa 1381 cttctgatcg gagtt.
```

The sequence obtained from Cat 2 is shown in SEQ ID NO:7. The new isolate was also detected in three other Swiss cats (cats 365102, 376660, and 408606). The complete 16S rRNA gene was sequenced for these three cats and the results shown in SEQ ID NO:8, SEQ ID NO:9 and SEQ ID NO:10, respectively. The new isolate was also detected in a wild-ranging Brazilian ocelot. The sequence of the 16S rRNA gene is shown in SEQ ID NO:11.

```
          GAACTGTC CAAAAGGCAG TTAGCGGCGA ACGGGTGAGT AATACATATT    SEQ ID NO:7

TAACATGCCC TCCGGAAGGA AATAGCCGTT CGAAAGAACG ATTAATGTCC

TATAGTATCC TCCATCAGAC AGAAGGGGGA TTTAAAGGTG AAAACCGCCG

GAGGATTGGA ATATGTCCTA TTAGCTAGTT GGCGGGATAA AAGCCCACCA

AGGCGATGAT AGGTAGCTGG TCTAAGAGGA TGAACAGCCA CAATGGGATT

GAGATACGGC CCATATTCCT ACGGGAAGCA GCAGTAGGGA ATCTTCCACA

ATGGGCGAAA GCCTGATGGA GCAATGCCAT GTGAACGATG AAGGCCAGAC

AGGTCGTAAA GTTCTTTTAG AGGGGAAAAA TTTGATGGTA CCCTCTGAAT

AAGTGACAGC AAATTATGTG CCAGCAGCTG CGGTAATACA TAGGTCGCGA

GCGTTATTCG GATTTATTGG GCGTAAAGCA AGCGCAGGCG GATGAATAAG

TTCTGCATTA AAAGCAGCTG CTTAACAGTT GTTTGTGCCG AATACTATTC

ATCTAGAATG TGGTAGGAAG TTTTGGAATT AAATATGGAG CGGTGGAATG

TGTAGATATA TTTAAGAACA CCAGAGGCGA AGGCGAAAAC TTAGGCCATT

ATTGACGCTT AGGCTTGAAA GTGTGGGTAG CAAATGGGAT TAGATACCCC

AGTAGTCCAC ACCGTAAACG ATGGGTATTA GATGTCGGGA TTTGTGTTTC

GGCGTTGTAG CTTACGTGTT AAATACCCCG CCTGGGTAGT ACATATGCAA

ATATGAAACT CAAAGGAGTT GACGGGACC TGAACAAGTG GTGGAACATG

TTGCTTAATT CGATAATACA CGAAAAACCT TACCAAGGTT TGACATCCTT

TGCAAAGCCA TAGAAATATG GTGGAGGTTA TCAGAGTGAC AGGTGGTGCA

TGGTTGTCGT CAGCTCGTGT CATGAGATGT TTGGTTAAGT CCCGCAACGA
```

```
GCGCAACCCT ACTCTTTAGT TGATTGTCTA AAGAGACTGA ACAGTAATGT

ATAGGAAGGA TGGGATCACG TCAAATCATC ATGCCCCTTA TGCCTTGGGC

CGCAAACGTG TTACAATGGT GAGTACAATG TGTCGCGAAC CAGCGATGGT

AAGCTAATCA CCAAAACTCA TCTCAGTCCG GATAAAAGGC TGCAATTCGC

CTTTTTGAAG TTGGAATCAC TAGTAATCCC GTGTCAGCTA TATCGGGGTG

AATACGTTCC CAGGTCTTGT ACACACCGCC CGTCAAACTA TGAGAGGAAG

GGGCATTTGA AAACACATTC AATTGTGTCA AGAATGAAAC TTC

GAACTGTCAA AAAGGCAGTT AGCGGCGAAC GGGTGAGTAA TACATATTTA    SEQ ID NO:8

ACATGCCCTC CGGAAGGAAA TAGCCGTTCG AAAGAACGAT TAATGTCCTA

TAGTATCCTC CATCAGACAG AAGGGGGATT TAAAGGTGAA AACCGCCGGA

GGATTGGAAT ATGTCCTATT AGCTAGTTGG CGGGATAAAA GCCCACCAAG

GCGATGATAG GTAGCTGGTC TAAGAGGATG AACAGCCACA ATGGGATTGA

GATACGGCCC ATATTCCTAC GGGAAGCAGC AGTAGGGAAT CTTCCACAAT

GGGCGAAAGC CTGATGGAGC AATGCCATGT GAACGATGAA GGCCAGACAG

GTCGTAAAGT TCTTTTAGAG GGGAAAAATT TGATGGTACC CTCTGAATAA

GTGACAGCAA ACTATGTGCC AGCAGCTGCG GTAATACATA GGTCGCGAGC

GTTATTCGGA TTTATTGGGC GTAAAGCAAG CGCAGGCGGA TGAATAAGTT

CTGCATTAAA AGCAGCTGCT TAACAGTTGT TTGTGCCGAA TACTATTCAT

CTAGAATGTG GTAGGAAGTT TTGGAATTAA ATATGGAGCG GTGGAATGTG

TAGATATATT TAAGAACACC AGAGGCGAAG GCGAAAACTT AGGCCATTAT

TGACGCTTAG GCTTGAAAGT GTGGGTAGCA AATGGGATTA GATACCCCAG

TAGTCCACAC CGTAAACGAT GGGTATTAGA TGTCGGGATT TGTGTTTCGG

CGTTGTAGCT TACGTGTTAA ATACCCCGCC TGGGTAGTAC ATATGCAAAT

ATGAAACTCA AAGGAATTGA CGGGGACCTG AACAAGTGGT GGAACATGTT

GCTTAATTCG ATAATACACG AAAAACCTTA CCAAGGTTTG ACATCCTTTG

CAAAGCCATA GAAATATGGT GGAGGTTATC AGAGTGACAG GTGGTGCATG

GTTGTCGTCA GCTCGTGTCA TGAGATGTTT GGTTAAGTCC CGCAACGAGC

GCAACCCTAC TCTTTAGTTG ATTGTCTAAA GAGACTGAAC AGTAATGTAT

AGGAAGGATG GGATCACGTC AAATCATCAT GCCCCTTATG CCTTGGGCCG

CAAACGTGTT ACAATGGTGA GTACAATGTG TCGCGAACCA GCGATGGTAA

GCTAATCACC AAAACTCATC TCAGTNNGGA TAAAAGGCTG CAATTCGCCT

TTTTGAAGTT GGAATCACTA GTAATCCCGT GTCAGNTATA TCGGGGTGAA

TACGTTCCCA GGTCTTGTAC ACACCGCCCG TCAAACTATG AGAGGAAGGG

GCATTTGAAA ACACATTCAA TTGTGTCAAG AATGAAACTT CT

CTATTTAGGT GACACTATAG AATACTCAAG CTATGCATCA AGCTTGGTAC    SEQ ID NO:9

CGAGCTCGGA TCCACTAGTA ACGGCCGCCA GTGTGCTGGA ATTCGCCCTT

GAACTGTCCA AAAGGCAGTT AGCGGCGAAC GGGTGAGTAA TACATATTTA

ACATGCCCTC CGGAAGGAAA TAGCCGTTCG AAAGAACGAT TAATGTCCTA

TAGTATCCTC CATCAGACAG AAGGGGGATT TAAAGGTGAA AACCGCCGGA

GGATTGGAAT ATGTCCTATT AGCTAGTTGG CGGGATAAAA GCCCACCAAG
```

-continued

```
GCGATGATAG GTAGCTGGTC TAAGAGGATG AACAGCCACA ATGGGATTGA
GATACGGCCC ATATTCCTAC GGGAAGCAGC AGTAGGGAAT CCTCCACAAT
GGGCGAAAGC CTGATGGAGC AATGCCATGT GAACGATGAA GGCCAGACAG
GTCGTAAAGT TCTTTTAGAG GGGAAAAATT TGATGGTACC CTCTGAATAA
GTGACAGCAA ACTATGTGCC AGCAGCTGCG GTAATACATA GGTCGCGAGC
GTTATTCGGA TTTATTGGGC GTAAAGCAAG CGCAGGCGGA TGAATAAGTT
CTGCATTAAA AGCAGCTGCT TAACAGTTGT TTGTGCCGAA TACTATTCAT
CTAGAATGTG GTAGGAAGTT TTGGAATTAA ATATGGAGCG GTGGAATGTG
TAGATATATT TAAGAACACC AGAGGCGAAG GCGAAAACTT AGGCCATTAT
TGACGCTTAG GCTTGAAAGT GTGGGTAGCA AATGGGATTA GATACCCCAG
TAGTCCGCAC CGTAAACGAT GGGTATTAGA TGTCGGGATT TGTGTTTCGG
CGTTGTAGCT TACGTGTTAA ATACCCCGCC TGGGTAGTAC ATATGCAAAT
ATGAAACTCA AAGGAATTGA CGGGGACCTG AACAAGTGGT GGAACATGTT
GCTTAATTCG ATAATACACG AAAAACCTTA CCAAGGTTTG ACATCCTTTG
CAAAGCCATA GAAATATGGT GGAGGTTATC AGAGTGACAG GTGGTGCATG
GTTGTCGTCA GCTCGTGTCA TGAGATGTTT GGTTAAGTCC CGCAACGAGC
GCAACCCTAC TCTTTAGTTG ATTGTCTAAA GAGACTGAAC AGTAATGTAT
AGGAAGGATG GGATCACGTC AAATCATCAT GCCCCTTATG CCTTGGGCCG
CAAACGTGTT ACAATGGTGA GTACAATGTG TCGCGAACCA GCGATGGTAA
GCTAATCACC AAAACTCATC TCAGTCCGGA TAAAAGGCTG CAATTCGCCT
TTTTGAAGTT GGAATCACTA GTAATCCCGT GTCAGCTATA TCGGGTGAA
TACGTTCCCA GGTCTTGTAC ACACCGCCCG TCAAACTATG AGAGGAAGGG
GCATTTGAAA ACACATTCAA TTGTGTCAAG AATGAAACTT CT
```

```
     GAACTG TCCAAAAGGC AGTTAGCGGC GAACGGGTGA GTAATACATA    SEQ ID NO:10
TTTAACATGC CCTCCGGAAG GAAATAGCCG TTCGAAAGAA CGATTAATGT
CCTATAGTAT CCTCCATCAG ACAGAAGGGG GATTTAAAGG TGAAAACCGC
CGGAGGATTG GAATATGTCC TATTAGCTAG TTGGCGGGAT AAAAGCCCAC
CAAGGCGATG ATAGGTAGCT GGTCTAAGAG GATGAACAGC CACAATGGGA
TTGAGATACG GCCCATATTC CTGCGGGAAG CAGCAGTAGG GAATCTTCCA
CAATGGGCGA AAGCCTGATG GAGCAATGCC ATGTGAACGA TGAAGGCCAG
ACAGGTCGTA AAGTTCTTTT AGAGGGGAAA AATTTGATGG TACCCTCTGA
ATAAGTGACA GCAAGCTATG TGCCAGCAGC TGCGGTAATA CATAGGTCGC
GAGCGTTATT CGGATTTATT GGGCGTAAAG CAAGCGCAGG CGGATGAATA
AGTTCTGCAT TAAAAGCAGC TGCTTAACAG TTGTTTGTGC CGAATACTAT
TCATCTAGAA TGTGGTAGGA AGTTTTGGAA TTAAATATGG AGCGGTGGAA
TGTGTAGATA TATTTAAGAA CACCAGAGGC GAAGGCGAAA ACTTAGGCCA
TTATTGACGC TTAGGCTTGA AAGTGTGGGT AGCAAATGGG ATTAGATACC
CCAGTAGTCC ACACCGTAAA CGATGGGTAT TAGATGTCGG GATTTGTGTT
TCGGCGTTGT AGCTTACGTG TTAAATACCC CGCCTGGGTA GTACATATGC
AAATATGAAA CTCAAAGGAA TTGACGGGGA CCTGAACAAG TGGTGGAACA
```

-continued

```
TGTTGCTTAA TTCGATAATA CACGAAAAAC CTTACCAAGG TTTGACATCC
TTTGCAAAGC CATAGAAATA TGGTGGAGGT TATCAGAGTG ACAGGTGGTG
CATGGTTGTC GTCAGCTCGT GTCATGAGAT GTTTGGTTAA GTCCCGCAAC
GAGCGCAACC CTACTCTTTA GTTGATTGTC TAAAGAGACT GAACAGTAAT
GTATAGGAAG GATGGGATCA CGTCAAATCA TCATGCCCCT TATGCCTTGG
GCCGCAAACG TGTTACAATG GTGAGTACAA TGTGTCGCGA ACCAGCGATG
GTAAGCTAAT CACCAAAACT CATCTCAGTC CGGATAAAAG GCTGCAATTC
GCCTTTTTGA AGTTGGAATC ACTAGTAATC CCGTGTCAGC TATATCGGGG
TGAATACGTT CCCAGGTCTT GTACACACCG CCCGTCAAAC TATGAGAGGA
AGGGGCATTT GAAAACACAT TCAATTGTGT CAAGAATGAA ACTTCT
GAATTCGCCC TTGAACTGTC CAAAAGGCAG TTAGCGGCGA ACGGGTGAGT    SEQ ID NO:11
AATACATATT TAACATGCCC TCCGGAAGGA ATAGCCGTT CGAAAGAACG
ATTAATGTCC TATAGTATCC TCCATCAGAC AGAAGGGGGA TTTAAAGGTG
AAAACCGCCG GAGGATTGGA ATATGTCCTA TTAGCTAGTT GGCGGGATAA
AAGCCCACCA AGGCGATGAT AGGTAGCTGG TCTAAGAGGA TGAACAGCCA
CAATGGGATT GAGATACGGC CCATATTCCT ACGGGAAGCA GCAGTAGGGA
ATCTTCCACA ATGGGCGAAA GCCTGATGGA GCAATGCCAT GTGAACGATG
AAGGCCAGAC AGGTCGTAAA GTTCTTTTAG AGGGGAAAAA TTTGATGGTA
CCCTCTGAAT AAGTGACAGC AAACTATGTG CCAGCAGCTG CGGTAATACA
TAGGTCGCGA GCGTTATTCG GATTTATTGG GCGTAAAGCA AGCGCAGGCG
GATGAATAAG TTCTGCATTA AAAGCAGCTG CTTAACAGTT GTTTGTGCCG
AATACTATTC ATCTAGAATG TGGTAGGAAG TTTTGGAATT AAATATGGAG
CGGTGGAATG TGTAGATATA TTTAAGAACA CCAGAGGNGA AGGCGAAAAC
TTAGGCCATT ATTGACGCTT AGGCTTGAAA GTGTGGGTAG CAAATGGGAT
TAGATACCCC AGTAGTCCAC ACCGTAAACG ATGGGTATTA GATGTCGGGA
TTTGTGTTTC GGCGTTGTAG CTTACGTGTT AAATACCCCG CCTGGGTAGT
ACATATGCAA ATATGAAACT CAAAGGAATT GATGGGACC TGAACAAGTG
GTGGAACATG TTGCTTAATT CGATAATACA CGAAAAACCT TACCAAGGCT
TGACATCCTT TGCAAAGCCA TAGAAATATG GTGGAGGTTA TCAGAGTGAC
AGGTGGTGCA TGGTTGTCGT CAGCTCGTGT CATGAGATGT TTGGTTAAGT
CCCGCAACGA GCGCAACCCT ACTCTTTAGT TGATTGTCTA AAGAGACTGA
ACAGTAATGT ATAGGAAGGA TGGGATCACG TCAAATCATC ATGCCCCTTA
TGCCTTGGGC CGCAAACGTG TTACAATGGT GAGTACAATG TGTCGCGAAC
CAGCGATGGT AAGCTAATCA CCAAAACTCA TCTCAGTCCG GATAAAAGGC
TGCAATTCGC CTTTTTGAAG TTGGAATCAC TAGTAATCCC GTGTCAGCTA
TATCGGGGTG AATACGTTCC CAGGTCTTGT ACACACCGCC CGTCAAACTA
TGAGAGGAAG GGGCATTTGA AAACACATTC AATTGTGTCA AGAATGAAAC
TTCTAAGGGC GAATTC
```

SEQ ID NO:12 represents a consensus sequence of SEQ ID NOs:5, 7, 8, 9, 10, 11, 15, 16, 17, 18, and 19. "N" stands for any nucleotide.

380 is C or T, the nucleotide at position 389 is A or G, the nucleotide at position the 423 is T or C, nucleotide at position 454 is A or G, the nucleotide at position 455 is C or T, the

```
   1 cagaattaac gctggtggca tgcctaatac atgcaagtcg agcgaantgt cnnaangnca   SEQ ID NO:12

61 nttagcggcg aacgggtgag taatacatat ttaacatgcc cnncggaagg aaatagccgt 121 tcgaaagaan gattaatgtc ctatagtatc nnnnnncana nagnangnng atttaaaggt 181 gnaaaccgcc gnnggattgg aatatgtcct attagctagt tggcgggnta aaagcccacc 241 aaggcnatga taggtagctg gtctaagagg atgaacagcc acaangggat tgagatacgg 301 cccatattcc tncgggaagc agcagtaggg aatcntccac aatggncgaa agnctgatgg 361 agcaatgcca tgtgaangan gaaggccana caggtcgtaa agttcttta gaggggaaaa 421 atntgatggt accctctgaa taagtgacag caanntatgt gccagcagct gcggtaatac 481 ataggtcgcg agcgttattc ggatttattg ggcgtaaagc aagcgcaggc ggatgaataa 541 gttctgcatt aaaagcagct gcttaacagt tgtttgtgcc gaatactatt catctagaat 601 gtggtagnaa gttttggaat taaatatgga gcggtggaat gtgtngatat atttaagaac 661 accagaggcg aaggcgaaaa cttaggccat tattgacgct taggcttgaa agtgtgggta 721 gcaaatggga ttagatacccc cagtagtccn caccgtaaac gatgggtatt agatgtcggg 781 anttgnnttt cggcgttgta gcttacgtgt taaataccc gcctgggtag tacatatgca 841 aatatgaaac tcaaaggant tganggggac ctgaacaagt ggtggaacat gttgcttaat 901 tcgataatac acgaaaaacc ttaccaaggn ttgacatcnt ntgcnaagcn atagaaatat 961 ngtggaggtt atcanantga caggtggtnc atggttgtcg tcagctcgtg tcatgagatg 1021 tttggttaag tcccgcaacg agcgcaaccc tactctttag ttnnttntct aaagagactg 1081 aacagtaatg tataggaagg atgggatcac gtcaaatcat catgccccctt atgccttggg 1141 cngcaaacgt gttacaatgg ngagtacaat gtgtngcnan ncagcgatgg naagcnaatc 1201 acnaaanctc ntctcagtcc ggataaaagg ctgcaattcg ccttttttgaa gttggaatca 1261 ctagtaatcc cgtgtcagct atatcggggt gaatacgttc ccaggtcttg tacacaccgc 1321 ccgtcaaact atgagaggaa ggngcatttn aaaacanatt naattgtgtc aagaatgaaa 1381 cttctgattg gagtt.
```

In one embodiment of the invention the nucleotide at position 47 is T or C, the nucleotide at position 52 is A or C or G, the nucleotide at position 53 can be A or absent, the nucleotide at position 58 is A or G, the nucleotide at position 61 is A or G, the nucleotide at position 102 is T or C, the nucleotide at position 103 is T or A or C, the nucleotide at position 130 is T or C, the nucleotide at position 151 is T or C, the nucleotide at position 152 is C or T, the nucleotide at position 153 is T or C, the nucleotide at position 154 is T or C, the nucleotide at position 155 is T or A or C, the nucleotide at position 156 is C or T, the nucleotide at position 159 is G or absent, the nucleotide at position 161 is A or C, the nucleotide at position 164 is G or A, the nucleotide at position 166 is A or G, the nucleotide at position 168 is G or A, the nucleotide at position 169 is G or A, the nucleotide at position 182 is C or A, the nucleotide at position 192 is A or G, the nucleotide at position 193 is G or A, the nucleotide at position 228 is G or A, the nucleotide at position 246 is A or G, the nucleotide at position 285 is C or T, the nucleotide at position 312 is A or G, the nucleotide at position 335 is T or C, the nucleotide at position 346 is G or A, the nucleotide at position 353 is C or T, the nucleotide at position 377 is T or C, the nucleotide at position nucleotide at position 608 is A or G, the nucleotide at position 645 is G or A, the nucleotide at position 750 is A or G, the nucleotide at position 782 is C or T, the nucleotide at position 786 is A or T, the nucleotide at position 787 is A or G, the nucleotide at position 859 is A or G, the nucleotide at position 864 is C or T, the nucleotide at position 930 is T or C, the nucleotide at position 939 is C or T, the nucleotide at position 941 is T or C, the nucleotide at position 945 is G or A, the nucleotide at position 950 is T or C, the nucleotide at position 961 is G or A, the nucleotide at position 975 is A or G, the nucleotide at position 977 is A or G, the nucleotide at position 989 is G or A, the nucleotide at position 1063 is G or A, the nucleotide at position 1064 is A or C or T, the nucleotide at position 1067 is T or G, the nucleotide at position 1142 is T or C, the nucleotide at position 1161 is C or T, the nucleotide at position 1175 is T or C, the nucleotide at position 1178 is G or A, the nucleotide at position 1180 is A or C, the nucleotide at position 1181 is T or C, the nucleotide at position 1191 is T or C, the nucleotide at position 1196 is C or T, the nucleotide at position 1203 is T or C, the nucleotide at position 1207 is G or A, the nucleotide at position $^{121}$I is G or A, the nucleotide at position 1343 is A or G, the nucleotide at position 1350 is A or G, the nucleotide at position 1357 is T or C, the nucleotide at position 1361 is A or C, or any combination thereof.

The sequences obtained were compared to known sequences held on the GenBank database and percentage similarity was calculated using GCG® Wisconsin Package® (Accelrys GmbH, Munich, Germany). The sequences were aligned to one another using CLUSTAL W according to the method of Thompson, et al. (Thompson et al. 1994. Nucleic Acids Res 22:4673-80). A phylogenetic tree was construction from 1,000 sets of bootstrapped data by the neighbor-joining method.

To clarify the phylogenetic relationship of this new isolate to other hemotropic mycoplasmal species, the complete 16S rRNA gene was amplified and sequenced. Comparison of the gene sequences obtained from the blood from Cats 1, 2 and 946 with those held on the GenBank database revealed highest similarity (92%) with the 16S rRNA gene of *Mycoplasma coccoides* (AY171918.1). Furthermore, high similarity was found with the 16S rRNA genes of *Mycoplasma haemomuris* (90%), *Mycoplasma haemofelis* (88%), *Mycoplasma haemocanis* (88%), *Mycoplasma haemolama* (83%), *Mycoplamsa wenyonii* (83%), 'Candidatus *Mycoplasma kahanei*' (83%), 'Candidatus *Mycoplasma haemominutum*' (83%), *Mycoplasma ovis* (83%), 'Candidatus *Mycoplasma haemoparvum*' (82%), *Mycoplasma suis* (82%), *Mycoplasma fastidiosum* (82%) and *Mycoplasma erythrodidelphis* (81%).

Figure 3:
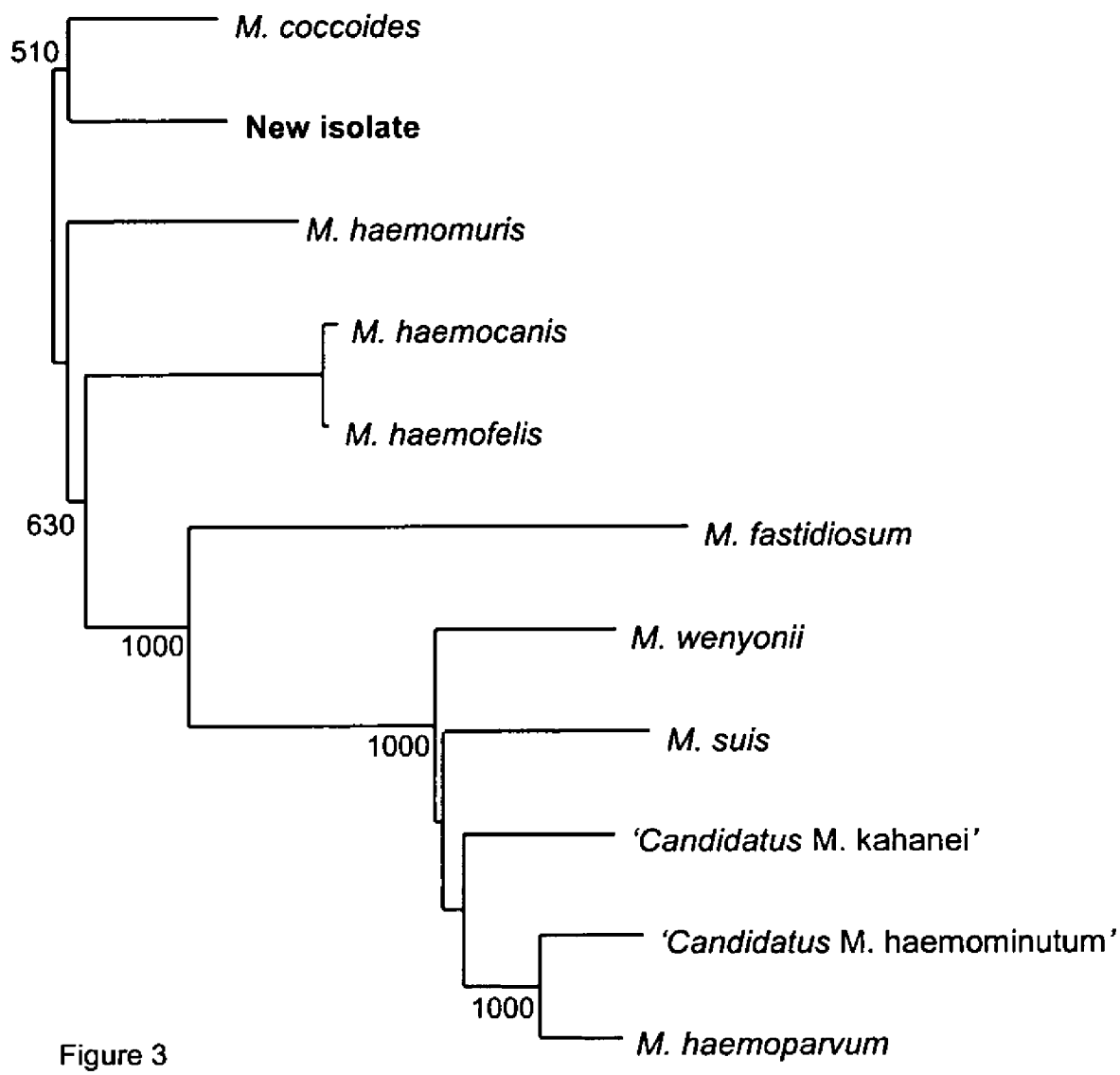
FIG. 3 shows the phylogenetic tree demonstrating the relationship of the new isolate to other hemoplasma species using a neighbor joining method. *M. coccoides* (AY171918), *M. haemomuris* (U82963), *M. haemocanis* (AY150973), *M. haemofelis* (AY150985), *M. fastidiosum* (AF125878), 'Candidatus *M. haemominutum*' (AY297712), 'Candidatus *M. kahanei*' (AF338269), 'Candidatus *M. haemoparvum*' (AY532390), *M. wenyonii* (AF016546) and *M. suis* (AY492086). The numbers at the nodes were generated from 1,000 Bootstrap resamplings; values <500 are not shown. The bar represents mean number of differences per 100 sites.

The sequences above were aligned to one another and to the 16S rRNA sequence of the new isolate and a phylogenetic tree was constructed (FIG. 3). This analysis confirmed the close relationship of the newly described feline hemoplasma isolate with *M. coccoides* and *M. haemomuris*, as these organisms formed a group that branches away from *M. haemofelis*. 'Candidatus *M. haemominutum*' was only distantly related to the new feline hemoplasma.

Development of a real-time PCR specific for the new hemoplasma isolate. To detect and quantify the new isolate in blood samples from naturally and experimentally infected cats, a specific quantitative PCR assay was established. Forward (5'-GAAGGCCAGACAGGTCGTAAAG-3') (SEQ ID NO:3) and reverse primers (5'-CTGGCACATAGTTWGCTGTCACTTA-3')(SEQ ID NO:4; W stands for A or T) and a probe (6-FAM-AAATTTGATGGTACCCTCTGA-MGB) (SEQ ID NO:6) were designed based on the 16S rRNA gene sequence (see above). The PCR reaction comprised 12.5 µl of 2xqPCR™ Mastermix (Eurogentec, Seraing, Belguim), 880 nM concentration of each primer, 200 nM of probe and 5 µl of template DNA, made up a final volume of 25 µl with water. Quantitative PCR reactions were performed using ABI PRISM® 7700 Sequence Detection system (Applied Biosystems). DNA samples from uninfected SPF cats and water were used as negative controls. For absolute quantification of the new isolate, plasmids containing the cloned 16S ribosomal DNA (rDNA) PCR product from the new isolate were generated and purified as described above and digested with Not1. Linearized DNA was quantified spectrophotometrically to calculate the copy number of plasmid present. The DNA template was then serially tenfold diluted in a solution of 30 µg/ml of salmon sperm DNA (Invitrogen), aliquoted and stored at −20° C. until use.

The correlation between packed cell volume (PCV) and copy number was calculated using a Spearman rank correlation test (Berkenkamp et al. 1998. Lab Anim Sci 38:398-401). A Wilcoxon signed ranks test was used to compare the hemoplasma loads of Cat 1 and 2 (Bland, 2000, An Introduction in Medical Statistics, 3$^{rd}$ ed. Oxford University Press, 217-222).

Further Sequencing

Additional isolates obtained from pet cats in Australia, South Africa and UK and from several wild felids were sequenced. Five 16S rRNA sequences (B3, D7, D9, G5 [from infected pet cats] and 94-100 [from a infected lion from the Serengeti]) that showed some differences as compared to the original isolate from Switzerland. The sequences exhibited 16 (G5) to 33 nucleotide differences (B3, D7, D9, 100-94) within the 1295 base pairs aligned to the published Swiss 'Candidatus *M. turicensis*' sequence (DQ157150/clone 2.24 from the Swiss prevalence study).

To amplify the 16S rRNA gene from D7 and D9, the following primers were used:

CMt_spec2f:
5'-CGA ATT GTC GAA AGA CAA TTA GC-3' SEQ ID NO:13

CMt-spec2r:
5'-AGA AGT TTC ATT CTT GAC ACA ATT TAA-3' SEQ ID NO:14

These primers are species specific and amplify a product of about 1342 nucleotides. The amplification was performed similarly to the amplifications described above.

```
                                            SEQ ID NO:15
B3 [Mycoplasma = Candidatus Mycoplasma turicensis]
Australian isolate B3, 16S ribosomal RNA gene,
partial sequence
CAGAATTAACGCTGGTGGCATGCCTAATACATGCAAGTCGAGCGAATTGT

CGAAAGACAATTAGCGGCGAACGGGTGAGTAATACATATTTAACATGCCC

CCCGGAAGGAAATAGCCGTTCGAAAGAACGATTAATGTCCTATAGTATCC

CCTTTCAGACAGAAAGGAGATTTAAAGGTGCAAACCGCCGAGGGATTGGA

ATATGTCCTATTAGCTAGTTGGCGGGATAAAAGCCCACCAAGGCAATGAT

AGGTAGCTGGTCTAAGAGGATGAACAGCCACAATGGGATTGAGATACGGC

CCATATTCCTACGGGAAGCAGCAGTAGGGAATCTTCCACAATGGACGAAA

GTCTGATGGAGCAATGCCATGTGAACGACGAAGGCCAGACAGGTCGTAAA

GTTCTTTTAGAGGGGAAAAATCTGATGGTACCCTCTGAATAAGTGACAGC

AAACTATGTGCCAGCAGCTGCGGTAATACATAGGTCGCGAGCGTTATTCG

GATTTATTGGGCGTAAAGCAAGCGCAGGCGGATGAATAAGTTCTGCATTA

AAAGCAGCTGCTTAACAGTTGTTTGTGCCGAATACTATTCATCTAGAATG

TGGTAGAAAGTTTTGGAATTAAATATGGAGCGGTGGAATGTGTGGATATA

TTTAAGAACACCAGAGGCGAAGGCGAAAACTTAGGCCATTATTGACGCTT

AGGCTTGAAAGTGTGGGTAGCAAATGGGATTAGATACCCCAGTAGTCCAC

ACCGTAAACGATGGGTATTAGATGTCGGGACTTGAGTTTCGGCGTTGTAG

CTTACGTGTTAAATACCCCGCCTGGGTAGTACATATGCAAATATGAAACT

CAAAGGAATTGACGGGGACCTGAACAAGTGGTGGAACATGTTGCTTAATT

CGATAATACACGAAAAACCTTACCAAGGTTTGACATCCTCTGCAAAGCTA

TAGAAATATAGTGGAGGTTATCAGAGTGACAGGTGGTGCATGGTTGTCGT

CAGCTCGTGTCATGAGATGTTTGGTTAAGTCCCGCAACGAGCGCAACCCT

ACTCTTTAGTTACTTGTCTAAAGAGACTGAACAGTAATGTATAGGAAGGA

TGGGATCACGTCAAATCATCATGCCCCTTATGCCTTGGGCCGCAAACGTG

TTACAATGGCGAGTACAATGTGTTGCAAACCAGCGATGGTAAGCCAATCA
```

```
CCAAAACTCGTCTCAGTCCGGATAAAAGGCTGCAATTCGCCTTTTTGAAG
TTGGAATCACTAGTAATCCCGTGTCAGCTATATCGGGGTGAATACGTTCC
CAGGTCTTGTACACACCGCCCGTCAAACTATGAGAGGAAGGAGCATTTAA
AAACATATTAAATTGTGTCAAGAATGAAACTTCTGATTGGAGTTAAGTCG
TAACAAGGTAGCGGATCCG
```

SEQ ID NO:16
D9 [Mycoplasma = Candidatus Mycoplasma turicensis]
Australian isolate D9, 16S ribosomal RNA gene,
partial sequence
```
GCGGCGAACGGGTGAGTAATACATATTTAACATGCCCCCCGGAAGGAAAT
AGCCGTTCGAAAGAACGATTAATGTCCTATAGTATCCCCTTTCAGACAGA
AAGGAGATTTAAAGGTGCAAACCGCCGAGGGATTGGAATATGTCCTATTA
GCTAGTTGGCGGGATAAAAGCCCACCAAGGCAATGATAGGTAGCTGGTCT
AAGAGGATGAACAGCCACAATGGGATTGAGATACGGCCCATATTCCTACG
GGAAGCAGCAGTAGGGAATCTTCCACAATGGACGAAAGTCTGATGGAGCA
ATGCCATGTGAACGACGAAGGCCAGACAGGTCGTAAAGTTCTTTTAGAGG
GGAAAAATCTGATGGTACCCTCTGAATAAGTGACAGCAAACTATGTGCCA
GCAGCTGCGGTAATACATAGGTCGCGAGCGTTATTCGGATTTATTGGGCG
TAAAGCAAGCGCAGGCGGATGAATAAGTTCTGCATTAAAAGCAGCTGCTT
AACAGTTGTTTGTGCCGAATACTATTCATCTAGAATGTGGTAGAAAGTTT
TGGAATTAAATATGGAGCGGTGGAATGTGTAGATATATTTAAGAACACCA
GAGGCGAAGGCGAAAACTTAGGCCATTATTGACGCTTAGGCTTGAAAGTG
TGGGTAGCAAATGGGATTAGATACCCCAGTAGTCCACACCGTAAACGATG
GGTATTAGATGTCGGGACTTGAGTTTCGGCGTTGTAGCTTACGTGTTAAA
TACCCCGCCTGGGTAGTACATATGCAAATATGAAACTCAAAGGAATTGAC
GGGGACCTGAACAAGTGGTGGAACATGTTGCTTAATTCGATAATACACGA
AAAACCTTACCAAGGTTTGACATCCTCTGCAAAGCTATAGAAATATAGTG
GAGGTTATCAGAGTGACAGGTGGTGCATGGTTGTCGTCAGCTCGTGTCAT
GAGATGTTTGGTTAAGTCCCGCAACGAGCGCAACCCTACTCTTTAGTTAC
TTGTCTAAAGAGACTGAACAGTAATGTATAGGAAGGATGGGATCACGTCA
AATCATCATGCCCCTTATGCCTTGGGCCGCAAACGTGTTACAATGGCGAG
TACAATGTGTTGCAAACCAGCGATGGTAAGCCAATCACCAAAACTCGTCT
CAGTCCGGATAAAAGGCTGCAATTCGCCTTTTTGAAGTTGGAATCACTAG
TAATCCCGTGTCAGCTATATCGGGGTAATACGTTCCCAGGTCTTGTACA
CACCGCCCGTCAAACTATGAGAGGAAGGAGCATTTAAAAACATA
```

SEQ ID NO:17
D7 [Mycoplasma = Candidatus Mycoplasma turicensis]
Australian isolate D7, 16S ribosomal RNA gene,
partial sequence
```
GCGGCGAACGGGTGAGTAATACATATTTAACATGCCCCCCGGAAGGAAAT
AGCCGTTCGAAAGAACGATTAATGTCCTATAGTATCCCCTTTCAGACAGA
AAGGAGATTTAAAGGTGCAAACCGCCGAGGGATTGGAATATGTCCTATTA
GCTAGTTGGCGGGATAAAAGCCCACCAAGGCAATGATAGGTAGCTGGTCT
AAGAGGATGAACAGCCACAATGGGATTGAGATACGGCCCATATTCCTACG
GGAAGCAGCAGTAGGGAATCTTCCACAATGGACGAAAGTCTGATGGAGCA
ATGCCATGTGAACGACGAAGGCCAGACAGGTCGTAAAGTTCTTTTAGAGG
GGAAAAATCTGATGGTACCCTCTGAATAAGTGACAGCAAACTATGTGCCA
GCAGCTGCGGTAATACATAGGTCGCGAGCGTTATTCGGATTTATTGGGCG
TAAAGCAAGCGCAGGCGGATGAATAAGTTCTGCATTAAAAGCAGCTGCTT
AACAGTTGTTTGTGCCGAATACTATTCATCTAGAATGTGGTAGAAAGTTT
TGGAATTAAATATGGAGCGGTGGAATGTGTAGATATATTTAAGAACACCA
GAGGCGAAGGCGAAAACTTAGGCCATTATTGACGCTTAGGCTTGAAAGTG
TGGGTAGCAAATGGGATTAGATACCCCAGTAGTCCACACCGTAAACGATG
GGTATTAGATGTCGGGACTTGAGTTTCGGCGTTGTAGCTTACGTGTTAAA
TACCCCGCCTGGGTAGTACATATGCAAATATGAAACTCAAAGGAATTGAC
GGGGACCTGAACAAGTGGTGGAACATGTTGCTTAATTCGATAATACACGA
AAAACCTTACCAAGGTTTGACATCCTCTGCAAAGCTATAGAAATATAGTG
GAGGTTATCAGAGTGACAGGTGGTGCATGGTTGTCGTCAGCTCGTGTCAT
GAGATGTTTGGTTAAGTCCCGCAACGAGCGCAACCCTACTCTTTAGTTAC
TTGTCTAAAGAGACTGAACAGTAATGTATAGGAAGGATGGGATCACGTCA
AATCATCATGCCCCTTATGCCTTGGGCCGCAAACGTGTTACAATGGCGAG
TACAATGTGTTGCAAACCAGCGATGGTAAGCCAATCACCAAAACTCGTCT
CAGTCCGGATAAAAGGCTGCAATTCGCCTTTTTGAAGTTGGAATCACTAG
TAATCCCGTGTCAGCTATATCGGGGTAATACGTTCCCAGGTCTTGTACA
CACCGCCCGTCAAACTATGAGAGGAAGGAGCATTTAAAAACATA
```

SEQ ID NO:18
G5 [Mycoplasma = Candidatus Mycoplasma turicensis]
South African isolate G5, 16S ribosomal RNA gene,
partial sequence
```
GAACTGTCCAAAAGGCAGTTAGCGGCGAACGGGTGAGTAATACATATTTA
ACATGCCCTACGGAAGGAAATAGCCGTTCGAAAGAACGATTAATGTCCTA
TAGTATCCTCCCTCAGACAGAAGGGGGATTTAAAGGTGAAAACCGCCGAA
GGATTGGAATATGTCCTATTAGCTAGTTGGCGGGATAAAAGCCCACCAAG
GCAATGATAGGTAGCTGGTCTAAGAGGATGAACAGCCACAACGGGATTGA
GATACGGCCCATATTCCTACGGGAAGCAGCAGTAGGGAATCTTCCACAAT
GGGCGAAAGCCTGATGGAGCAATGCCATGTGAATGATGAAGGCCAGACAG
GTCGTAAAGTTCTTTTAGAGGGGAAAAATCTGATGGTACCCTCTGAATAA
GTGACAGCAAACTATGTGCCAGCAGCTGCGGTAATACATAGGTCGCGAGC
GTTATTCGGATTTATTGGGCGTAAAGCAAGCGCAGGCGGATGAATAAGTT
CTGCATTAAAAGCAGCTGCTTAACAGTTGTTTGTGCCGAATACTATTCAT
CTAGAATGTGGTAGGAAGTTTTGGAATTAAATATGGAGCGGTGGAATGTG
TAGATATATTTAAGAACACCAGAGGCGAAGGCGAAAACTTAGGCCATTAT
TGACGCTTAGGCTTGAAAGTGTGGGTAGCAAATGGGATTAGATACCCCAG
TAGTCCACACCGTAAACGATGGGTATTAGATGTCGGGATTTGTGTTTCGG
CGTTGTAGCTTACGTGTTAAATACCCCGCCTGGGTAGTACATATGCAAAT
ATGAAACTCAAAGGAATTGACGGGGACCTGAACAAGTGGTGGAACATGTT
```

-continued

GCTTAATTCGATAATACACGAAAAACCTTACCAAGGTTTGACATCCTTTG

CAAAGCCATAGAAATATGGTGGAGGTTATCAGAGTGACAGGTGGTGCATG

GTTGTCGTCAGCTCGTGTCATGAGATGTTTGGTTAAGTCCCGCAACGAGC

GCAACCCTACTCTTTAGTTGCTTTTCTAAAGAGACTGAACAGTAATGTAT

AGGAAGGATGGGATCACGTCAAATCATCATGCCCCTTATGCCTTGGGCCG

CAAACGTGTTACAATGGTGAGTACAATGTGTCGCAACCCAGCGATGGCAA

GCTAATCACTAAAGCTCATCTCAGTCCGGATAAAAGGCTGCAATTCGCCT

TTTTGAAGTTGGAATCACTAGTAATCCCGTGTCAGCTATATCGGGGTGAA

TACGTTCCCAGGTCTTGTACACACCGCCCGTCAAACTATGAGAGGAAGGG

GCATTTGAAAACACATTCAATTGTGTCAAGAATGAAACTTC

SEQ ID NO:19
94-100 [Mycoplasma = Candidatus Mycoplasma
turicensis] African isolate 94-100, 16S ribosomal
RNA gene, partial sequence
TTGAACTGTCCAAAAGGCAGTTAGCGGCGAACGGGTGAGTAATACATATT

TAACATGCCCTTCGGAAGGAAATAGCCGTTCGAAAGAATGATTAATGTCC

TATAGTATCTTTCCCCAAAAGGAGGAAGATTTAAAGGTGAAAACCGCCGA

AGGATTGGAATATGTCCTATTAGCTAGTTGGCGGGGTAAAAGCCCACCAA

GGCGATGATAGGTAGCTGGTCTAAGAGGATGAACAGCCACAATGGGATTG

AGATACGGCCCATATTCCTACGGGAAGCAGCAGTAGGGAATCTTCCACAA

TGGGCGAAAGCCTGATGGAGCAATGCCATGTGAACGATGAAGGCCAAACA

GGTCGTAAAGTTCTTTTAGAGGGGAAAAATCTGATGGTACCCTCTGAATA

AGTGACAGCAAACTATGTGCCAGCAGCTGCGGTAATACATAGGTCGCGAG

CGTTATTCGGATTTATTGGGCGTAAAGCAAGCGCAGGCGGATGAATAAGT

TCTGCATTAAAAGCAGCTGCTTAACAGTTGTTTGTGCCGAATACTATTCA

TCTAGAATGTGGTAGAAAGTTTTGGAATTAAATATGGAGCGGTGGAATGT

GTAGATATATTTAAGAACACCAGAGGCGAAGGCGAAAACTTAGGCCATTA

TTGACGCTTAGGCTTGAAAGTGTGGGTAGCAAATGGGATTAGATACCCCA

GTAGTCCACACCGTAAACGATGGGTATTAGATGTCGGGATTTGAATTTCG

GCGTTGTAGCTTACGTGTTAAATACCCCGCCTGGGTAGTACATATGCAAA

TATGAAACTCAAAGGAATTGACGGGACCTGAACAAGTGGTGGAACATGT

TGCTTAATTCGATAATACACGAAAAACCTTACCAAGGTTTGACATCTTTT

GCGAAGCTATAGAAATATAGTGGAGGTTATCAAAATGACAGGTGGTACAT

GGTTGTCGTCAGCTCGTGTCATGAGATGTTTGGTTAAGTCCCGCAACGAG

CGCAACCCTACTCTTTAGTTATTTGTCTAAAGAGACTGAACAGTAATGTA

TAGGAAGGATGGGATCACGTCAAATCATCATGCCCCTTATGCCTTGGGCT

GCAAACGTGTTACAATGGCGAGTACAATGTGTCGCAAATCAGCGATGGTA

AGCTAATCACTAAAACTCGTCTCAGTCCGGATAAAAGGCTGCAATTCGCC

TTTTTGAAGTTGGAATCACTAGTAATCCCGTGTCAGCTATATCGGGTGA

ATACGTTCCCAGGTCTTGTACACACCGCCCGTCAAACTATGAGAGGAAGG

GGCATTTAAAAACACATTCAATTGTGTCAAGAATGAAACTTCT

We claim:

1. A purified nucleic acid molecule consisting of SEQ ID NO: 3 or 4 and optionally an isotopic label, non-isotopic label, a catalyst label, an enzyme label, a promoter label, a dye label, a fluorescent molecule, a chemiluminescent label, a coenzyme, an enzyme substrate, a radioactive group, a small organic molecule, an amplifiable polynucleotide sequence label, a particle label, a metal sol label, a crystallite label, a liposome label, a cell label, or a colorimetric label.

2. A method for detecting the presence or absence of a hemoplasma agent in a subject comprising detecting a nucleic acid molecule encoding the 16S rRNA in a sample obtained from the subject, wherein the detecting comprises use of the purified nucleic acid molecule of claim 1, and wherein the presence of a nucleic acid molecule encoding the 16S rRNA indicates the presence of the hemoplasma agent.

3. A method of claim 2, wherein the detecting comprises amplifying a 16 S rRNA nucleic acid molecule of the hemoplasma agent by a method selected from the group consisting of: polymerase chain reaction (PCR); ligase chain reaction; nucleic acid sequence-based amplification; self-sustained sequence replication; strand displacement amplification; branched DNA signal amplification; nested PCR; multiplex PCR; quantitative PCR; direct detection, in situ hybridization; Transcription Mediated Amplification (TMA); Rolling Circle Amplification (RCA); and Q-beta-replicase system.

4. A method of detecting 16 S rRNA nucleic acid molecules of a hemoplasma agent in a sample comprising:
   amplifying the 16S rRNA nucleic acid molecules of the hemoplasma agent using a first amplification primer consisting of SEQ ID NO:3 and a second amplification primer consisting of SEQ ID NO:4 ;
   and detecting an amplification product, wherein if an amplification product is detected, the 16S rRNA nucleic acid molecule is present.

5. The method of claim 4, wherein the quantity of the 16S rRNA nucleic acid molecules in the sample is determined.

6. The method of claim 4, wherein the first or second or both amplification primers further comprise a label.

7. The method of claim 6, wherein the label is a fluorescent moiety.

8. The method of claim 4, wherein the amplifying comprises real-time quantitative PCR and further comprises using a DNA polymerase with 5' nuclease activity and at least one probe comprising a detectable label.

9. The method of claim 8, wherein the at least one probe consists of SEQ ID NO:6.

10. The method of claim 4, wherein the amplifying comprises real-time quantitative PCR and further comprises using a detectable dye that binds to double-stranded DNA.

11. The method of claim 10, wherein the detectable dye is syber-green or ethidium bromide.

12. A method for detecting and quantifying nucleic acid molecules of a hemoplasma agent comprising:
   amplifying a 16S rRNA sequence of the hemoplasma agent using a first primer consisting of SEQ ID NO:3 ; a second primer consisting of SEQ ID NO:4 ; a DNA polymerase comprising 5' nuclease activity; a nucleic acid probe comprising nucleic acids complementary to the 16S rRNA sequence and comprising a reporter fluorescent dye and a quencher dye; wherein the nucleic acid from the hemoplasma agent is detected and quantified.

13. A kit for detecting a nucleic acid molecule, comprising purified nucleic acid molecules consisting of SEQ ID NO:3 and consisting of SEQ ID NO:4.

14. The kit of claim 13, further comprising a polymerase and one or more buffers.

15. The kit of claim 13, wherein the purified nucleic acid molecules comprise one or more labels.

16. The kit of claim 15, wherein the one or more labels comprise a fluorescent moiety.

17. An isolated hemoplasma agent deposited as ATCC PTA-6782.

18. An isolated hemoplasma agent, wherein a polymerase chain reaction (PCR) performed using nucleic acids of the hemoplasma agent with PCR primers consisting of SEQ ID NO:3 and SEQ ID NO:4 results in an amplification product, and wherein the hemoplasma agent comprises a 16S rRNA sequence of SEQ ID NO:12.

* * * * *